United States Patent
Kin et al.

(10) Patent No.: US 7,494,962 B2
(45) Date of Patent: Feb. 24, 2009

(54) SOLVENTS CONTAINING CYCLOAKYL ALKYL ETHERS AND PROCESS FOR PRODUCTION OF THE ETHERS

(75) Inventors: Idan Kin, Ottawa (CA); Genichi Ohta, Tokyo (JP); Kazuo Teraishi, Tokyo (JP); Kiyoshi Watanabe, Tokyo (JP)

(73) Assignee: Zeon Corporation, Tokyo (JP)

( * ) Notice: Subject to any disclaimer, the term of this patent is extended or adjusted under 35 U.S.C. 154(b) by 349 days.

(21) Appl. No.: 10/481,340

(22) PCT Filed: Jun. 27, 2002

(86) PCT No.: PCT/JP02/06501

§ 371 (c)(1),
(2), (4) Date: Sep. 24, 2004

(87) PCT Pub. No.: WO03/002500

PCT Pub. Date: Jan. 9, 2003

(65) Prior Publication Data

US 2005/0065060 A1    Mar. 24, 2005

(30) Foreign Application Priority Data

| Jun. 28, 2001 | (JP) | 2001-196766 |
| Oct. 30, 2001 | (JP) | 2001-332009 |
| Dec. 11, 2001 | (JP) | 2001-377483 |
| Mar. 29, 2002 | (JP) | 2002-094269 |
| Apr. 25, 2002 | (JP) | 2002-123832 |

(51) Int. Cl.
    *C11D 7/50* (2006.01)
(52) U.S. Cl. .................. 510/175; 510/407
(58) Field of Classification Search ............ 510/175, 510/407
See application file for complete search history.

(56) References Cited

U.S. PATENT DOCUMENTS 3,496,223 A * 2/1970 Mitchell et al. ............... 562/22

(Continued)

FOREIGN PATENT DOCUMENTS

EP     587434 A1    3/1994

(Continued)

OTHER PUBLICATIONS

Edited by Kagaku Daijiten Henshu Iinkai, "Kagaku Daijiten 9", Kyoritsu Shuppan Co., Ltd., Aug. 25, 1962, p. 437, "Yozai".

(Continued)

*Primary Examiner*—Gregory E Webb
(74) *Attorney, Agent, or Firm*—Birch, Stewart, Kolasch & Birch, LLP

(57) ABSTRACT

The present inventions are (A) a solvent comprising at least one cycloalkyl alkyl ether (1) represented by the general formula: R1-O—R2 (wherein R1 is cyclopentyl or the like; and R2 is C1-10 alkyl or the like); (B) a method of preparations the ethers (1) characterized by reacting an alicyclic olefin with an alcohol in the presence of an acid ion-exchange resin having a water content of 5 wt % or less. The solvent is useful as cleaning solvent for electronic components, precision machinery components or the like, reaction solvent using various chemical reactions, extraction solvent for extracting objective organic substances, solvent or remover for electronic and electrical materials, and so on. The process enables industrially advantageous production of the objective cycloalkyl alkyl ethers (1).

13 Claims, 2 Drawing Sheets

U.S. PATENT DOCUMENTS

| | | | |
|---|---|---|---|
| 4,306,100 A | 12/1981 | Wood | |
| 4,511,488 A | 4/1985 | Matta | |
| 4,640,719 A | 2/1987 | Hayes et al. | |
| 4,740,247 A | 4/1988 | Hayes et al. | |
| 4,762,826 A * | 8/1988 | Eckhardt | 514/63 |
| 4,990,688 A * | 2/1991 | Gosch et al. | 568/810 |
| 5,284,986 A * | 2/1994 | Dessau | 585/318 |
| 5,393,766 A * | 2/1995 | Hubele | 514/365 |
| 5,529,874 A | 6/1996 | Kobayashi et al. | |
| 5,589,503 A * | 12/1996 | Mencke et al. | 514/450 |
| 6,084,144 A * | 7/2000 | Takashima et al. | 585/525 |

FOREIGN PATENT DOCUMENTS

| | | |
|---|---|---|
| EP | 0 994 089 A1 | 4/2000 |
| GB | 2017693 A | 10/1979 |
| JP | 55-149219 A | 11/1980 |
| JP | 58-118531 A | 7/1983 |
| JP | 59-025345 A | 2/1984 |
| JP | 61-249945 A | 11/1986 |
| JP | 3-062897 A | 3/1991 |
| JP | 3-240754 A | 10/1991 |
| JP | 5-163188 A | 6/1993 |
| JP | 6-49495 A | 2/1994 |
| JP | 11-228478 A | 8/1999 |
| JP | 2001-261592 A | 9/2001 |
| JP | 2002-167347 A | 6/2002 |
| WO | 98/51651 A1 | 11/1998 |

OTHER PUBLICATIONS

Edited by Shigeru Ozaki, "Shokubai Kogaku Koza 10 Genso Betsu Shokubai Binran", Chijinshokan Co., Ltd., Feb. 25, 1967, pp. 727 to 729.

* cited by examiner

SOLVENTS CONTAINING CYCLOAKYL ALKYL ETHERS AND PROCESS FOR PRODUCTION OF THE ETHERS

TECHNICAL FIELD

The present invention relates to a solvent comprising a cycloalkyl alkyl ether compound and a process for producing the cycloalkyl alkyl ether compound. More particularly, the present invention relates to a solvent containing a cycloalkyl alkyl ether compound useful as a cleaning solvent for electronic parts, precision machinery components, and the like, a reaction solvent for various chemical reactions, an extraction solvent for extracting objective organic substances from various mixtures, a solvent or remover agent for electronic and electric materials, and the like, to a method for cleaning articles, a method for reacting an organic metal, a Grignard reaction method, a method for extracting organic compounds, and a method for producing parts for electronic and electrical materials using the solvent, and to a process for advantageously producing the cycloalkyl alkyl ether compound in an industrial scale.

BACKGROUND ART

Conventionally, a cleaning operation using a cleaning solvent is carried out during manufacturing electronic equipment, precision machines, and the like to prevent degradation of electrical characteristics and mechanical characteristics. Chemically stable chlorine or flon solvents have been used for this purpose. The use of a number of these solvents has been regulated due to the problems in safety, toxicity, and environmental pollution.

Cleaning solvents and cleaning compositions that are safe, less toxic, and less pollutant to the environment have been proposed as substitutes for these solvents. For example, cleaning solvents and cleaning compositions described in U.S. Pat. Nos. 4,511,488, 4,640,719, 4,740,247, JP-A 3-62897, JP-A 6-49495, and the like are given.

However, these cleaning solvents are not necessarily satisfactory in their detergency, particularly detergency for oils and fats. Therefore, development of a novel cleaning solvent excelling in both safety and detergency has been desired.

Conventionally, ether solvents that are non-protonic and polar have widely been used as reaction solvents for various organic reactions (hereinafter referred to as "reaction") such as a Grignard reaction. Tetrahydrofuran (THF), which is a typical ether solvent, is a non-protonic and polar solvent having a moderate boiling point. THF is commonly used as a reaction solvent, particularly for Grignard reactions, reactions using an organolithium compound or the like, and other similar reactions. However, if THF is used as a solvent for a reaction mixture to which water is added, it is difficult to remove THF from the reaction mixture since THF is mutually soluble with water and forms an azeotrope. A special distillation process involving addition of an entrainer or other third components is required for industrially separating one component from another in an azeotrope. The distillation unit, which must be equipped with at least two columns and auxiliary equipment such as a decanter, can be operated only with difficulty requiring a high cost.

When THF is used as a reaction solvent for Grignard reaction in which a Grignard reagent such as phenyl magnesium bromide (PhMgBr) is reacted with a ketone that can be easily enolated such as acetone, a self-aldol condensation reaction which is a side reaction is predominant over the target nucleophilic reaction, producing the target reaction product (α,α-dimethylbenzyl alcohol) only in a low yield. Therefore, development of a reaction solvent that can be easily recovered after use and exhibits excellent reaction selectivity has been desired.

A solvent extraction is a well-known method for extracting a desired compound from a mixture using an appropriate extraction solvent. Various extraction solvents that can be used are known. Examples include halogenated hydrocarbons such as dichloromethane and chloroform; aliphatic hydrocarbons such as n-hexane and cyclohexane; aromatic hydrocarbons such as benzene and toluene; esters such as methyl acetate and ethyl acetate; ketones such as acetone and cyclohexanone; and ethers such as diethyl ether and dipropyl ether.

Requirements for the extraction solvents include (i) being inactive under the extraction conditions, (ii) being capable of sufficiently dissolving extracted substances, (iii) having an appropriate boiling point, producing vapor that has a minimal risk of being absorbed during the solvent extraction operation, and being easily evaporated, and (iv) having only a slight possibility of polluting the environment.

However, only a few extraction solvents currently available satisfy these requirements. For example, since halogenated hydrocarbons such as dichloromethane and chloroform having excellent capability of dissolving various organic compounds have a strong toxicity and a low boiling point, their vapor have a risk of being inhaled during the extraction operation and cause an environmental pollution problem. Esters such as ethyl acetate and aromatic hydrocarbons such as toluene are also extraction solvents with wide versatility, but exhibit only limited capability of dissolving organic compounds having a moderate polarity and insufficient extraction efficiency. Therefore, development of a novel extraction solvent advantageous from the viewpoint of extraction operation and environmental safety has been desired.

Conventionally, various organic solvents such as aromatic hydrocarbon solvents, aliphatic hydrocarbon solvents, and halogenated hydrocarbon solvents have been used as a solvent and parting agents for electronic materials, electrical materials, and the like. It is desirable that these solvents and parting agents exhibit high solubility and dispersibility of electronic and electrical materials and are safe and free from the problem of environmental pollution.

However, not a few currently available solvents and parting agents lack solubility and dispersibility of electronic and electrical materials, are strongly toxic, and pollute the environment. Therefore, development of a solvent and parting agent exhibiting high solubility and dispersibility of electronic and electrical materials and being safe and free from the problem of environmental pollution has been desired.

As the method for producing ethers by the addition reaction of an olefin to an alcohol, a method of using crystalline alumino silicate as a catalyst (Japanese Patent Application Laid-open No. 59-25345), a method of using HZSM-5 zeolite as a catalyst U.S. Pat. No. 4,306,100), a method of using special alumino silicate having many acid points on the surface as a catalyst (Japanese Patent Application Laid-open No. 61-249945), a method of using tungsten oxide in which the crystal water possessed by a heteropoly acid has been adjusted to about 3.0 or less molecules per one molecules of the heteropolyacid as a catalyst (Japanese Patent Application Laid-open No. 5-163188), and the like are known.

However, the activity of the catalysts used in these methods has been insufficient to manufacture the target compound at an industrially acceptable selectivity and conversion rate, particularly to manufacture a cycloalkyl alkyl ether compound from an alicyclic olefin as a starting raw material.

A method of using an acidic ion-exchange resin is an old method for producing ethers by the addition reaction of an olefin to an alcohol. However, the method involves problems such as isomerization of olefins as a side reaction and thermal instability of used resins if conventional acidic ion-exchange resins are used as described in Japanese Patent Application Laid-open No. 5-163188, for example.

The present invention has been achieved in view of this situation. A first object of the present invention is therefore to provide (a) a novel cleaning solvent that can be safely handled, can be mixed with many organic solvents and dissolve various pollutant organic substances such as fats and oils, waxes, and natural resins, and can be promptly decomposed in the atmosphere without adversely affecting the ozone layer, (b) a reaction solvent that can be easily recovered after use and exhibits excellent reaction selectivity, (c) an extraction solvent advantageous from the viewpoint of operational efficiency and environmental safety, (d) a solvent for electronic and electrical materials exhibiting high solubility and dispersibility of the materials and being safe and free from the problem of environmental pollution, and (e) a solvent usable as a parting agent used for removing a photosensitive layer from an OPC (Organic Photo Conductor) drum or for removing semiconductor materials and the like glued to jigs with an adhesive from the adhesive or the jig.

A second object of the present invention is to provide an industrially advantageous process for producing a cycloalkyl alkyl ether compound useful as such a cleaning solvent, reaction solvent, extraction solvent, parting agent for electronic or electrical materials.

DISCLOSURE OF THE INVENTION

Figure 1:
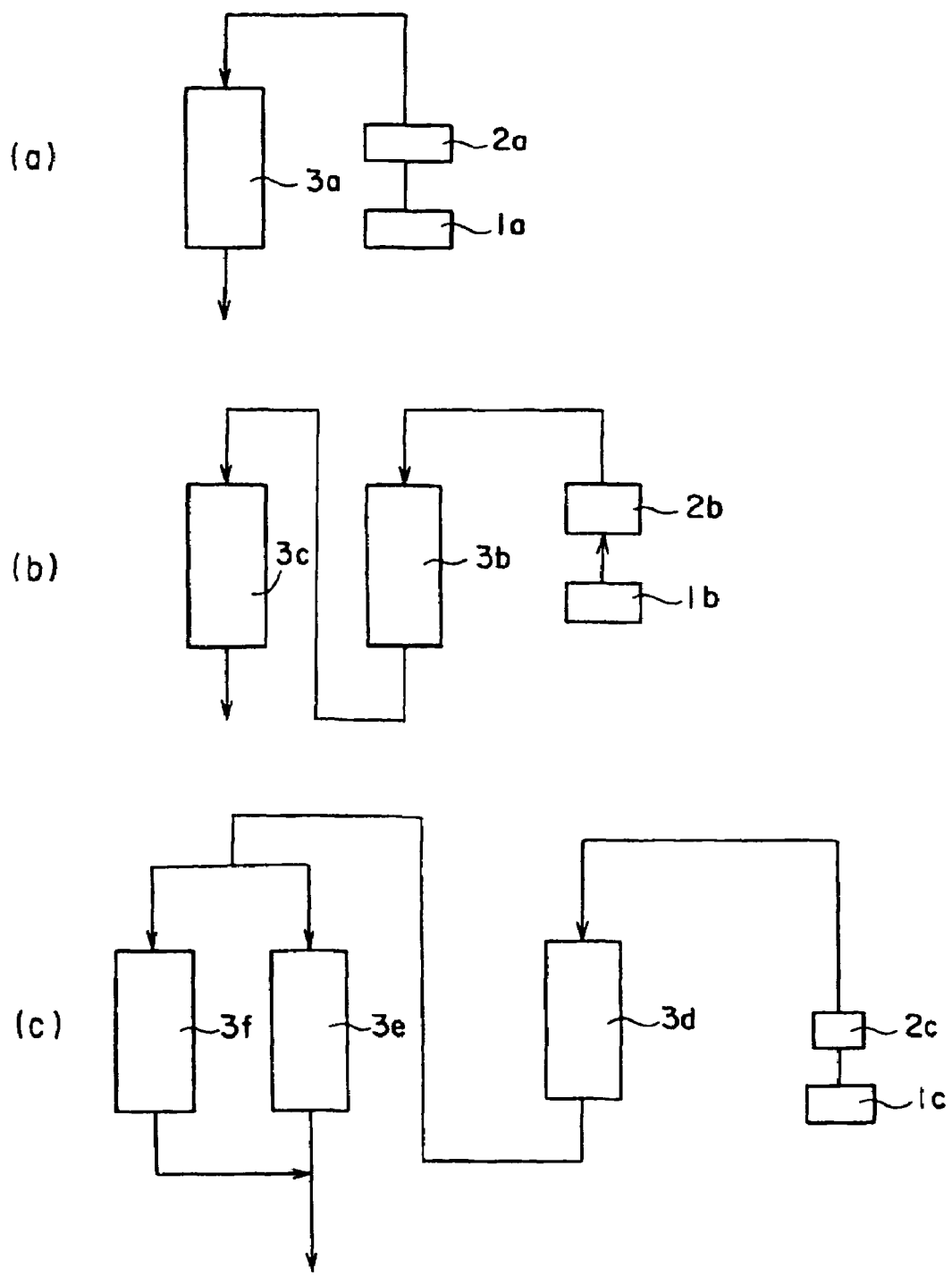
FIG. 1 is a drawing illustrating a reactor used for the manufacturing process of the present invention.

The present inventors have found that cycloalkyl alkyl ether compounds (1) has a moderate boiling point, can be safely handled, can be promptly decomposed in the atmosphere without adversely affecting the ozone layer, and can be mixed with many organic solvents, exhibiting excellent solubility to fats and oils, waxes, natural resins, and the like, (2) can be used as a reaction solvent that can be easily recovered after use and can produce the target product in a high yield when used as an organic synthetic chemical reaction such as a Grignard reaction, (3) can be used as an extraction solvent advantageous from the viewpoint of operational efficiency and environmental safety, (4) can be used as a solvent for electronic and electrical materials exhibiting high solubility and dispersibility to the materials, exhibiting least toxicity, and being almost free from the problem of environmental pollution, and (5) can be used as a parting agent exhibiting excellent solubility to sensitizers, organic adhesives, photo resists, and organic insulating materials, exhibiting least toxicity, and being almost free from the problem of environmental pollution.

The present inventors have found that the target cyclopentyl methyl ether can be obtained at a high selectivity and high conversion rate if cyclopentene as an alicyclic olefin is reacted with methanol as an alcohol in the presence of an acidic ion-exchange resin catalyst with a water content of 5 wt % or less. The inventors have continued the studies based on this finding and completed the present invention.

Specifically, the present invention provides, in the first place, a solvent comprising at least one cycloalkyl alkyl ether compound represented by the formula (1): $R^1$—O—$R^2$, wherein $R^1$ represents a cyclopentyl group or cyclohexyl group which may have a substituent and $R^2$ represents an alkyl group having 1-10 carbon atoms or a cycloalkyl group having 3-8 carbon atoms which may have a substituent.

In the present invention provides, the cycloalkyl alkyl ether compound represented by the formula (1) is preferably a cycloalkyl alkyl ether compound represented by the formula (2): $R^1$—O—$R^3$, wherein $R^1$ is the same as defined above and $R^3$ represents an alkyl group having 1-10 carbon atoms or a cycloalkyl group having 3-8 carbon atoms and, more preferably, a cycloalkyl alkyl ether compound represented by the formula (3): $R^4$—O—$R^3$, wherein $R^4$ is a cyclopentyl group and $R^3$ is the same as defined above.

The solvent of the present invention is preferably a cleaning solvent, a reaction solvent, an extraction solvent, a solvent for electronic and electrical materials, or a parting solvent. When the solvent of the present invention is reaction solvent, the reaction is preferably an organometallic reaction or a Grignard reaction.

It is preferable that the water content of the solvent of the present invention be 100 ppm or less, with a further preferable solvent comprising an antioxidant.

In the second place, the present invention provides an organometallic reaction method using the solvent of the present invention.

In the third place, the present invention provides a Grignard reaction method using the solvent of the present invention.

In the fourth place, the present invention provides a method for extracting an organic compound using the solvent of the present invention.

In the fifth place, the present invention provides a method for cleaning articles using the solvent of the present invention.

In the sixth place, the present invention provides a method for manufacturing electronic and electrical components using the solvent of the present invention.

In the seventh place, the present invention provides a process for producing a cycloalkyl alkyl ether compound of the formula (1), (2), or (3) comprising reacting an alicyclic olefin with an alcohol in the presence of an acidic ion-exchange resin having a water content of 5 wt % or less.

BEST MODE FOR CARRYING OUT THE INVENTION

1) Solvent Comprising a Cycloalkyl Alkyl Ether Compound

The solvent of the present invention comprises one or more types of cycloalkyl alkyl ether compounds shown by the above formula (1), preferably formula (2), and even more preferably formula (3) (hereinafter simply referred to as "cycloalkyl alkyl ether compound" from time to time).

(A) Cycloalkyl Alkyl Ether Compound

In the cycloalkyl alkyl ether compound shown by the above formulas (1) and (2), $R^1$ represents a cyclopentyl group which may have a substituent or a cyclohexyl group which may have a substituent.

As examples of the substituent group, an alkyl group having 1-4 carbon atoms, alkoxy group having 1-4 carbon atoms, alkylthio group having 1-4 carbon atoms, and halogen atom can be given. Of these, an alkyl group having 1-4 carbon atoms is preferable, with a methyl group or ethyl group being particularly preferable.

As specific examples of $R^1$, a cyclopentyl group or cyclohexyl group; an alkyl cyclopentyl group or alkyl cyclohexyl group such as 2-methyl-cyclopentyl group, 3-ethyl-cyclohexyl group, 3-sec-butyl-cyclopentyl group, and 2-tert-butyl-cyclohexyl group; an alkoxy cyclopentyl group or alkoxy cyclohexyl group such as 3-methoxy-cyclopentyl group, 3-ethoxy-cyclohexyl group, 2-sec-butoxy-cyclopentyl group, and 3-tert-butoxy-cyclohexyl group; an alkyl thiocyclopentyl group or alkyl thiocyclohexyl group such as 3-methylthio-cyclopentyl group, 3-ethylthio-cyclohexyl group, 2-sec-butylthio-cyclopentyl group, and 3-tert-butylthio-cyclohexyl group; and a halogenated cyclopentyl group or halogenated cyclohexyl group such as 2-chloro-cyclopentyl group, 3-chloro-cyclopentyl group, 2-bromo-cyclohexyl group, and 3-bromo-cyclohexyl group can be given.

In the cycloalkyl alkyl ether compound shown by the above formula (1), $R^2$ represents an alkyl group having 1-10 carbon atoms which may have a substituent or a cycloalkyl group having 3-8 carbon atoms which may have a substituent.

As specific examples of $R^2$, an alkyl group having 1-10 carbon atoms such as a methyl group, ethyl group, n-propyl group, isopropyl group, n-butyl group, sec-butyl group, tert-butyl group, n-pentyl group, neopentyl group, n-hexyl group, n-heptyl group, n-octyl group, n-nonyl group, and n-decyl group; a cycloalkyl group having 3-8 carbon atoms such as a cyclopropyl group, cyclobutyl group, cyclopentyl group, cyclohexyl group, cycloheptyl group, and cyclooctyl group; an alkoxyalkyl group such as a methoxymethyl group, 1-methoxyethyl group, 2-ethoxy-tert-butyl group, and 2-ethoxy-n-hexyl group; an alkoxycycloalkyl group such as a 2-methoxy-cyclopropyl group and 3-ethoxy-cyclohexyl group; an alkyl thioalkyl group such as a methyl thiomethyl group, 1-methyl thioethyl group, 2-methylthio-tert-butyl group, and 4-methylthio-n-hexyl group; an alkyl thiocloalkyl group such as a 2-methylthio-cyclopropyl group and 3-ethylthio-cyclohexyl group; a halogenated alkyl group such as a chloromethyl group, bromomethyl group, 1-chloroethyl group, 2-bromo-tert-butyl group, and 2-chloro-n-hexyl group; and a halogenated cycloalkyl group such as a 2-chloro-cyclopropyl group and 3-bromo-cyclohexyl group can be given.

In the cycloalkyl alkyl ether compound shown by the above formulas (2) and (3), $R^3$ represents an alkyl group having 1-10 carbon atoms or a cycloalkyl group having 3-8 carbon atoms.

As specific examples of $R^3$, an alkyl group having 1-10 carbon atoms such as a methyl group, ethyl group, n-propyl group, isopropyl group, n-butyl group, sec-butyl group, tert-butyl group, n-pentyl group, neopentyl group, n-hexyl group, n-heptyl group, n-octyl group, n-nonyl group, and n-decyl group, and a cycloalkyl group having 3-8 carbon atoms such as cyclopropyl group, cyclobutyl group, cyclopentyl group, cyclohexyl group, cycloheptyl group, and cyclooctyl group can be given.

In the present invention, $R^4$ represents a cyclopentyl group.

In the present invention, of the cycloalkyl alkyl ether compounds shown by the above formula (1), in view of cleaning effect, environmental safety, reaction selectability, extraction effect, volatility, chemical stability, and production cost, the cycloalkyl alkyl ether compounds shown by the above formula (2) are preferable, with the cycloalkyl alkyl ether compounds shown by the above formula (3) being particularly preferable.

In the present invention, of the cycloalkyl alkyl ether compounds shown by the above formula (3), the cycloalkyl alkyl ether compound wherein $R^4$ is an alkyl group having 1-4 carbon atoms or a cycloalkyl group having 3-6 carbon atoms is preferable, with cyclopentyl methyl ether (hereinafter, abbreviated as "CPME"), cyclopentyl ethyl ether, or dicyclopentyl ether being even more preferable, and CPME being particularly preferable.

(B) Method for Producing Cycloalkyl Alkyl Ether Compound

Cycloalkyl alkyl ether compounds are well known in the art and can be produced by known methods.

Specific examples of such a method include (a) a method of reacting a cyclopentyl alcohol which may have a substituent the same as that possessed by the group $R^1$ (hereinafter referred to as "a cyclopentyl alcohol") or a cyclohexyl alcohol which may have a substituent the same as that possessed by the group $R^1$ (hereinafter referred to as "a cyclohexyl alcohol") with an alkylating agent in the presence of a base or (b) a method of reacting a cyclopentene which may have a substituent the same as that possessed by the group $R^1$ (hereinafter referred to as "cyclopentenes") or a cyclohexene which may have a substituent the same as that possessed by the group $R^1$ (hereinafter referred to as "cyclohexenes") with a compound represented by the formula R'—OH, wherein R' represents a hydrogen atom and an alkyl group having 1-10 carbon atoms which may have a substituent the same as that possessed by the group R or a cycloalkyl group having 3-8 carbon atoms which may have a substituent the same as that possessed by the group $R^2$ in the presence of a solid acid. Of these, method (b) is preferable due to lower cost and the unnecessary consumption of a large quantity of a base.

As examples of the alkylating agent used in method (a), halogenated alkyl, dialkyl sulfuric acid, alkyl sulfonate, and the like can be given. The alkylating agent is usually used in an amount of 0.9-10 mol and preferably 1.1-5.0 mol for 1 mol of the cyclopentyl alcohol or cyclohexyl alcohol.

As examples of the base used in the alkylating reaction, a metal hydride, alkali metal, carbonate, hydrogen carbonate, organic base, and the like can be given. The base is usually used in an amount of 1-10 mols and preferably 1-5 mols for 1 mol of the cyclopentyl alcohol or cyclohexyl alcohol.

The method (a) can be carried out either without using a solvent or using an inert solvent. The reaction in the presence of an inert solvent is more preferable. A non-protonic polar solvent is preferably used.

Either commercially available cyclopentyl alcohols and cyclohexyl alcohols or those produced by a known method can be used as the raw materials.

The alkylation reaction can be carried out by a method of suspending or dissolving a prescribed amount of a base to an inert solvent, adding a cyclopentyl alcohol or cyclohexyl alcohol, and further adding an alkylating agent, a method of adding a prescribed amount of a base to a solution of a cyclopentyl alcohol or cyclohexyl alcohol in an inert solvent and adding a prescribed amount of an alkylating agent, and the like.

In these instances, after adding the base and before adding the alkylating agent, it is preferable to form a cyclopentyl alcohol or cyclohexyl alcohol salt by stirring and heating the reaction mixture. The reaction is usually carried out at a temperature ranging from room temperature to the boiling point of the solvent used for several minutes to several hours.

In the method of (b), cyclopentenes or cyclohexenes is caused to come in contact with the compound shown by the formula R'OH in the presence of a solid acid.

As specific examples of the cyclopentenes, cyclopentene, 1-methylcyclopentene, 3-methylcyclopentene, 1,3-dimethylcyclopentene, 1-fluorocyclopentene, and 1-phenylcyclopentene can be given. As examples of cyclohexenes, cyclohexene, 1-methylcyclohexene, 4-methylcyclohexene, 1,3-dimethylcyclohexene, 1-fluorocyclohexene, 4-chlorocyclohexene, 1-phenylcyclohexene, and 4-phenylcyclohexene can be given. Of these, cyclopentene or cyclohexene are preferable, with cyclopentene being particularly preferable.

As specific examples of the compounds shown by the formula R'OH, water, methanol, ethanol, 2-methoxyethanol, n-propanol, 2-chloro-n-propanol, isopropanol, n-butanol, 3-methylthio-h-butanol, 2-bromo-n-butanol, sec-butanol, isobutanol, tert-butanol, n-pentanol, n-hexanol, cyclopropyl alcohol, cyclopentyl alcohol, 2-chlorocyclopentyl alcohol, cyclohexyl alcohol, cycloheptanol, and cyclooctanol can be given.

The compound shown by the formula R'OH is usually used in an amount of 0.002-11 mol, and preferably 0.02-7 mol, for 1 mol of cyclopentenes (cyclohexenes). The reaction is usually carried out at 50-200° C., and preferably at 80-180° C.

As examples of the solid acid used in the method (b), an acidic ion exchange resin or crystalline solid acid can be given, with an acidic ion exchange resin being preferable.

The acidic ion-exchange resin is an insoluble porous synthetic resin comprising a polymer matrix having a fine three-dimensional network structure and acidic ion-exchange groups and is commonly called a cationic exchange resin.

As examples of the acidic ion-exchange resin, a strongly acidic cation-exchange resin comprising a styrene polymer substrate and sulfonic acid groups as ion-exchange groups and a weakly acidic cation-exchange resin comprising an acrylic or methacrylic polymer matrix and acrylic or methacrylic acid groups as ion-exchange groups can be given. The acidic ion-exchange resins are broadly classified into a gel type, porous type, and high porous type from the viewpoint of a geometrical structure. Any types can be used in the present invention.

As specific preferable examples of the acidic ion-exchange resin, styrene based strongly acidic cation-exchange resin gel DIAION SK1B, SK012, SK104, SK106, SK110, SK112, and SK116 (manufactured by Mitsubishi Chemical Corp.); porous styrene based strongly acidic cation-exchange resin PK208, PK212, PK216, PK220, and PK228 (manufactured by Mitsubishi Chemical Corp.); highly porous styrene based strongly acidic cation-exchange resin HPK25 (manufactured by Mitsubishi Chemical Corp.); heat resistant styrene based strongly acidic cation-exchange resin RCP145 (manufactured by Mitsubishi Chemical Corp.); acrylic acid based and methacrylic acid based weakly acidic cation-exchange resin WK10, WK11, WK100, WT01S, WK40 (manufactured by Mitsubishi Chemical Corp.); sulfonic acid based cation-exchange resin UBK530, UBK550, UBK535, and UBK555 (manufactured by Mitsubishi Chemical Corp.); SPC type styrene based acidic cation-exchange resin SPC108 and SPC118; strongly acidic Bayer catalyst gel K1221, K1431, K1481, and K1491 (manufactured by Bayer); macroporous strongly acidic Bayer catalyst K2431, K2621, and K2641 (manufactured by Bayer); Amberlite (XE-284) (manufactured by Rohm and Haas), and Amberlyst 15 (manufactured by Organo Corporation) can be given.

Of these, from the viewpoint of easy availability and easy handling, a sulfonic acid-type strong acid cation exchange resin comprising a sulfonic acid group as the ion-exchange group is preferable, with a sulfonic acid-type styrene strong acid cation exchange resin comprising a copolymer of styrene or halogenated styrene and divinyl benzene as the polymer substrate and a sulfonic acid group as the ion-exchange group being particularly preferable.

The apparent density(g/L-R) of the acidic ion-exchange resin is usually 500-1,000, and preferably 600-900. The water content before drying is usually 30-70 wt %. There are no specific limitations to the average particle size of the acidic ion-exchange resin. The particle size, which is appropriately determined based on the inner diameter of the reaction tube used in the additional reaction mentioned later on, is usually in the range of 0.02-10 mm, and preferably 0.5-2 mm. Usually, a common proton-type acidic ion-exchange resin is used and can be recycled using common methods for repeated use.

Of these acidic ion-exchange resins, the acidic ion-exchange resins comprising water in an amount of 5 wt % or less, preferably 3 wt % or less, and particularly preferably 2 wt % or less are preferably used as the acidic ion-exchange resin of the present invention. The target cycloalkyl alkyl ether compound can be obtained at a high selectivity and high conversion rate by using the acidic ion-exchange resin containing water in an amount of 5 wt % or less as a reaction catalyst.

To obtain the acidic ion-exchange resin comprising water in an amount of 5 wt % or less, the resin is dried before use to remove the water. There are no specific restrictions to the method for drying the acidic ion-exchange resin as long as the acidic ion-exchange resin comprising 5 wt % or less of water after drying can be obtained.

A common method of dehydration with heating can be used as the method of drying. As examples of the heat dehydration method, (i) a method wherein the acidic ion-exchange resin is placed in a common dryer and heated at 50-120° C., and preferably 80-100° C., for several minutes to several hours; (ii) a method wherein the acidic ion-exchange resin is heat dried under a circulation of an inert gas at a prescribed temperature (about 100° C. above room temperature) for several minutes to several hours; and (iii) a combination of the methods (i) and (ii) can be given.

As examples of the inert gas, air, nitrogen, argon, helium, hydrogen, aliphatic hydrocarbon, and aromatic hydrocarbon can be given. There are no specific restrictions to the speed at which the inert gas is circulated. The hourly space velocity on a gaseous basis at heating temperature inside the apparatus is usually 0.01-100 vol/Hr•vol.

When an acidic ion-exchange resin comprising 5 wt % or less of water is used, an ether compound can be produced by contacting an alicyclic olefin other than the above-mentioned cyclopentene (cyclohexene) with the compound shown by the formula R'OH.

As examples of the alicyclic olefin, an aliphatic compound having a monocyclic or polycyclic structure with 3-20 carbon atoms and having at least one carbon-carbon double bond in the cyclic skeleton, excluding cyclopentenes and cyclohexenes, can be given. Furthermore, alicyclic olefins comprising substituents such as an alkyl group, aryl group, halogen atom, nitro group, amino group, alkoxy group, sulfone group, and cyano group on the cyclic skeleton may be used. As examples of other alicyclic olefins, seven-membered cyclic compounds such as cycloheptene, 1-methyl cycloheptene, and 1-phenyl cycloheptene; and eight-membered cyclic compounds such as cyclooctene, 1-methyl cyclooctene, and 1-phenyl cyclooctene can be given.

There are no specific limitations to the method for contacting the cyclopentenes (cyclohexenes) with the compound of the formula R'OH in the presence of the acidic ion-exchange resin. As examples of this method, a method of adding the acidic ion-exchange resin to a mixture of cyclopentenes (cyclohexenes) and the compound of the formula R' OH (hereinafter, also referred to as "mixture") while stirring (batch type) and a method comprising filling a column with the acidic ion-exchange resin and flowing the mixture through the column (hereinafter referred to as "reaction column") (flow type) can be given. Of these, from the viewpoint of efficient and continuous purification of the reaction product, use of the flow type is preferable.

In the production of the above-mentioned mixture, the cyclopentenes (cyclohexenes) and the compound shown by the formula R'OH are mixed at a predetermined ratio. In this instance, the mixture comprising cyclopentenes (cyclohexenes) and the compound of the formula R'OH can be prepared beforehand, stored in a tank, and sent to the column in a gaseous or liquid state, or cyclopentenes (cyclohexenes) and the compound shown by the formula R'OH can be stored in separate tanks, sent to the column separately in a liquid state, and mixed immediately before entering the column. The mixture preferably contains as little water as possible to ensure efficient production of the target product. The mixture preferably contains water in an amount of 1 wt % or less, with 500 ppm or less being particularly preferable.

In the batch-type, the acidic ion-exchange resin, cyclopentenes (cyclohexenes), and the compound shown by the formula R'OH are added to the reactor in predetermined amounts and the reaction mixture is stirred at a predetermined temperature and pressure. In this instance, the acidic ion-exchange resin is usually used in an amount of 0.01-200 parts by weight, preferably 0.1-150 parts by weight, and particularly preferably 1-100 parts by weight for 100 parts by weight of cyclopentenes (cyclohexenes).

In the batch-type, even though there are no specific limitations to the proportion of cyclopentenes (cyclohexenes) and the compound shown by the formula R'OH, the compound shown by the formula R'OH is preferably used in an excessive proportion. Since the mixture is heated for a long period of time in the batch-type, a polymer of cyclopentenes (cyclohexenes) may be produced if an excessive amount of cyclopentenes (cyclohexenes) is used. The proportion of cyclopentenes (cyclohexenes) and the compound shown by the formula R'OH (the mol ratio of (cyclopentenes (cyclohexenes)/(compound shown by the formula R'OH)) is usually 1/1-1/50, preferably 1/1-1/30, and particularly preferably 1/1-1/20.

When the flow-type is used, the mixture is flowed through the reaction column. In this instance, the column possessing a heating apparatus is used and the mixture is flowed through the reaction column heated to the prescribed temperature (reaction temperature). Even though the mixture may be flowed through the reaction column in a liquid or gaseous state, the mixture is preferably flowed through the reaction column in a gaseous state to obtain high selectivity and a high conversion rate of the target product.

When the mixture is flowed through the reaction column in a gaseous state, a gaseous phase-solid phase reaction occurs. As an example of a method for conducting this reaction, as shown in FIG. 1(a), a method wherein the mixture liquid exits from the mixture liquid storage tank 1a, is transformed into a gas by the heat/gasification device 2a, and enters the reaction column 3a in a gaseous state can be given. When several reaction columns are used, the pipes connecting the reaction columns, in addition to the reaction columns, are preferably maintained at the prescribed temperature.

As specific examples of the flow-type, a method of using a reaction column 3a packed with the acidic ion-exchange resin as shown in FIG. 1(a), a method of using a plurality of reaction columns 3b and 3c packed with the acidic ion-exchange resin and connected in series as shown in FIG. 2(b), and a method of using a plurality of reaction columns 3d, 3e, and 3f connected in series and in parallel as shown in FIG. 1(c) can be given. When several columns are used in combination, the conversion rate of cyclopentenes [(cyclohexenes) or the compound of the formula R'OH] can be improved.

There are no specific limitations to the size of the columns used. The size may be selected in accordance with the scale of the reaction. When a combination of several reaction columns is used, the type of the acidic ion-exchange resin packed in each of the columns may be the same or different.

Figure 2:
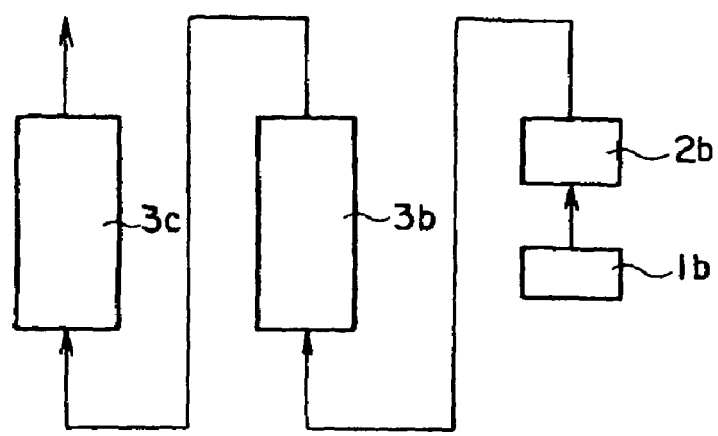
FIG. 2 is a drawing illustrating a reactor used for the manufacturing process of the present invention.

As the method for flowing the mixture through the reaction columns packed with the acidic ion-exchange resin, a down flow-type wherein the mixture is flowed from the top of the reaction columns 3b and 3c as shown in FIG. 1(b) or an up flow-type wherein the mixture is flowed from the bottom of the reaction columns 3b and 3c as shown in FIG. 2 can be used. From the viewpoint of high conversion rate and selectivity of the target product, the down flow-type is preferable.

The mixture passes through the reaction column usually at a pressure of 30 MPa above the atmospheric pressure, with 10 MPa above the atmospheric pressure being preferable and 5 MPa above the atmospheric pressure being particularly preferable. When the flow-type is used, the space velocity of the liquid mixture (LHSV) is usually 0.01-100 $hr^{-1}$, and preferably 0.1-20 $hr^{-1}$, and that of the gaseous state mixture (GHSV) is usually 0.01-40,000 $hr^{-1}$, and preferably 0.1-8,000 $hr^{-1}$. When several reaction columns are used, the reaction temperature, flow speed, and the like may be different for each reaction column.

In the flow-type, even though there are no specific limitations to the proportion of the cyclopentenes (cyclohexenes) and the compound of the formula R'OH, the cyclopentenes (cyclohexenes) is preferably used in an excessive amount. Since the mixture is heated for only a short period of time in the flow-type, polymerization of the cyclopentenes (cyclohexenes) does not occur, on the other hand, the amount of dialkyl ether by-products increases when the compound of the formula R'OH is used in an excessive amount. The proportion of the cyclopentenes (cyclohexenes) and the compound of the formula R'OH (the mol ratio of (cyclopentenes (cyclohexenes)/(compound of the formula R'OH)) is usually 1/3-20/1, preferably 1/3-10/1, more preferably 1/3-5/1, and particularly preferably 1/3-3/1.

Figure 3:
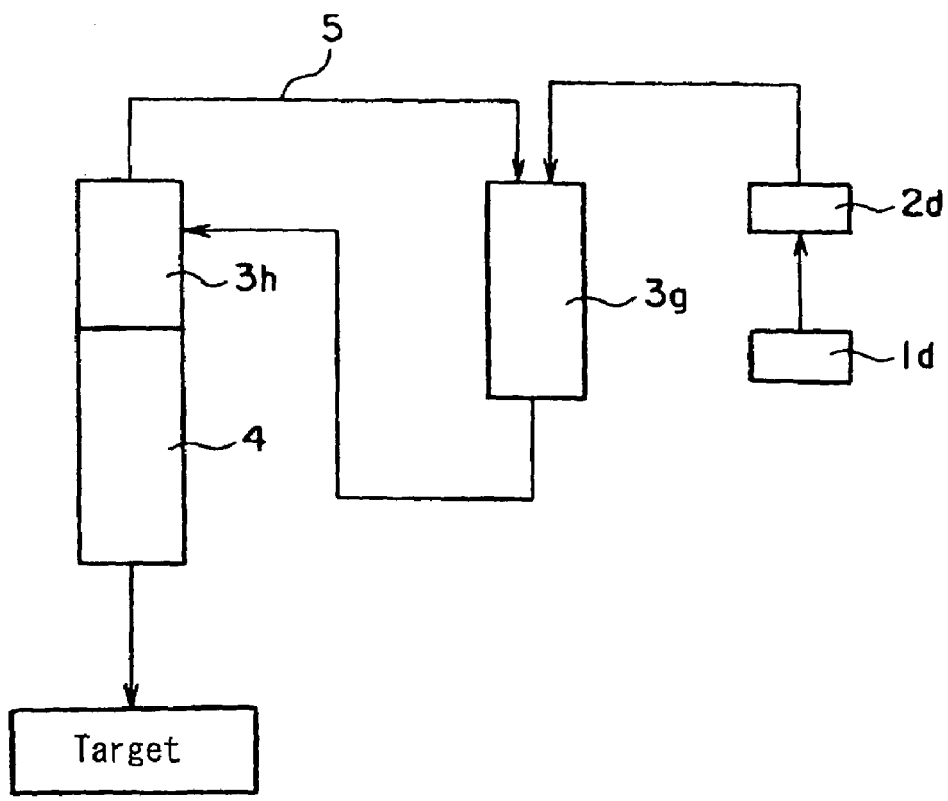
FIG. 3 is a drawing illustrating an apparatus combining a reactor and distillatory used for the manufacturing process of the present invention.

After the reaction, the targeted cycloalkyl alkyl ether compound can be isolated from the react-ion liquid by using common isolation and purification methods such as solvent extraction and distillation. Distillation may be conducted several times. Distillation devices known in the art such as a continuous rectification device comprising a rectification column can be used. It is also possible, as shown in FIG. 3, to circulate the mixture through a reaction column 3g packed with an acidic ion-exchange resin, cause the resulting reaction mixture to pass through a reaction column 3h, and continuously distill the mixture using a distillation apparatus 4 packed with Rashich rings. In this method, the unreacted alicyclic olefin and alcohol can be returned to the reaction column 3g by the pipe 5 and reacted once again to obtain a high conversion rate of the target product.

In the above production method (b), a solid acid in crystalline form (crystalline solid acid) may be used as the solid acid. The crystalline solid acid is a general term for acidic inorganic substances in which silicon, phosphorus, aluminum oxide, and the like form specific chemical constitution unit and form unit with regularity and includes naturally occurring zeolite, synthetic zeolite, and the like. Acidic or neutral zeolites are preferable as the crystalline solid acid. These zeolites may be used as a mixture. As examples of such a zeolite, ZSM-type zeolite such as H-ZSM-5 and Na-ZSM-5; faujasite such as Na—Y-type zeolite, H—Y-type zeolite, K—Y-type zeolite, Na—X-tyep zeolite, and 13X-type zeolite; H-mordenite, Na-mordenite, molecular sieve 3A, molecular sieve 4A, and molecular sieve 5A; and metallo alumino silicate or metallo silicate containing hetero atoms such as boron, iron, gallium, titanium, copper, or silver can be given. In addition, Si-substituted aluminum phosphate zeolite (SAPO) having a a phosphoric acid skeleton can also be used. Either commercially available products or products produced by a known method may be used.

Although zeolites with a proton type cationic moiety are usually used, those with a cationic moiety replaced with at least one of the elements selected from the group consisting of alkaline earth metals such as Mg, Ca, and Sr, rare earth elements such as La and Ce, and elements in the groups 8-10 in the periodic table such as Fe, Co, Ni, Ru, Pd, and Pt, or those containing Ti, Zr, Hf, Cr, Mo, W, Th, or the like can also be used.

Various types of zeolite can be appropriately selected according to the molecular size of the cycloalkyl alkyl ether compounds to be produced. Of these various types of zeolite, molecular sieve 3A, molecular sieve 4A, molecular sieve 5A, H-mordenite, Na-mordenite, ZSM-5, and the like are preferable. H-mordenite, Na-mordenite, ZSM-5, and the like are more preferable, with the H-type zeolite having a penta-sil structure being still more preferable, and ZSM-series zeolite being particularly preferable. The pore diameter of zeolite used is usually 2-12 Å, and preferably 2-10 Å. Although there are no specific limitations to the composition of zeolite, those having silica/alumina molar ratio of 10 or more are preferable, with those having silica/alumina molar ratio of 20 or more being still more preferable.

There are no specific limitations to the form of the crystalline solid acid. Any crystalline solid acid in the form of powder, particles, or formed solid acids may be used. Primary particles in powdery crystalline solid acid has a diameter preferably or 1 μm or less. The primary particles may be independently present or may be present as secondary aggregates. The particle or formed solid acids may have a spherical, disk-like, column-like, or cylindrical outward configuration. The average particle size of the particle or formed solid acids is not specifically limited and can be appropriately selected from the range usually of 1-40 mm, and preferably of 2-20 mm. The specific surface area can be appropriately selected from the range usually of 1-100 $m^2/g$ without any specific limitations.

The crystalline solid acid is usually used in an amount of 0.001-200 parts by weight, preferably 0.1-200 parts by weight, and more preferably 1.0-150 parts by weight for 100 parts by weight of the cyclopentenes (cyclohexenes).

Any reactors commonly used in the industry such as a fluid bed-type reactor, a batch-type reactor, and a fixed-bed flow-type reactor can be applied to using crystalline solid acid. In the case of a batch-type reactor, any conventionally known stirrer such as a vibration-type and rotation-type can be used for stirring the mixture inside the reactor. The number of vibration, number of rotation, and stirring rate can be appropriately determined. In the case of the fixed-bed flow-type reactor, a formed catalyst manufactured by extrusion molding or compression molding is preferably used. The LHSV (Liquid Hourly Space Velocity) is usually in the range of 0.1-5.0 $h^{-1}$, and preferably 0.5-3.0 $h^{-1}$.

The above production method (b) may be carried out without using a solvent or using an inert solvent that does not mix with water, in which case the raw material cyclopentene compounds or cyclohexene compounds are diluted with the inert solvent. As examples of the solvent, aliphatic saturated hydrocarbons such as n-butane, n-pentane, n-hexane, n-heptane, n-octane, n-nonane, and n-decane; aromatic hydrocarbons such as benzene, toluene, ethyl benzene, xylene, anisol, cumene, and nitrobenzene; alicyclic saturated hydrocarbons such as cyclopentane, alkyl-substituted cyclopentane, alkoxy-substituted cyclopentane, nitro-substituted cyclopentane, cyclohexane, alkyl-substituted cyclohexane, alkoxy-substituted cyclohexane, nitro-substituted cyclohexane, cycloheptane, alkyl-substituted cycloheptane, alkoxy-substituted cycloheptane, nitro-substituted cycloheptane, cyclooctane, alkyl-substituted cyclooctane, alkoxy-substituted cyclooctane, and nitro-substituted cyclooctane; nitrogen, argon, air, and helium can be given. The amount of the diluent used can be selected without any particular limitations as long as the reaction is not hindered. The solvent is used in an amount of usually 10-90 vol % and preferably 20-80 vol % of the total amount of the reaction liquid.

(C) Solvent Containing Cycloalkyl Alkyl Ether Compound

The solvent of the present invention comprises at least one type of cycloalkyl alkyl ether compound. The cycloalkyl alkyl ether compound is included in an amount of usually 30 wt % or more, and preferably 50 wt % or more of the total amount of the solvent.

The solvent of the present invention may comprise one or more types of other liquid organic compounds in addition to the cycloalkyl alkyl ether compound. As examples of the other liquid organic compound, aliphatic hydrocarbons such as n-pentane, n-hexane, n-heptane, n-octane, n-nonane, and n-decane; alicyclic hydrocarbons such as cyclopentane, cyclohexane, and cyclooctane; aromatic hydrocarbons such as benzene, toluene, and xylene; alcohols such as methanol, ethanol, n-propanol, isopropanol, n-butanol, and carbitol; ethers such as diethyl ether, diisopropyl ether, dibutyl ether, tetrahydrofuran, monoglyme, diglyme, 1,2-dimethoxyethane, and dioxane; ketones such as acetone, methylethyl ketone, 2-pentanone, 3-pentanone, cyclopentanone, and cyclohexanone; esters such as formate and acetate; nitriles such as acetonitrile; amides such as N,N-dimethyl formamide, N,N-dimethyl acetoamide, hexamethyl phosphoric acid triamide, and N-methylpyrrolidone; organic nitrogen compounds such as nitrobenzene; organic sulfur compounds such as dimethyl sulfoxide and sulfolane; organosilicon compounds such as tetramethylsilane, tetraethylsilane, methoxytrimethylsilane, ethoxytrimethylsilane, hexamethyldisiloxane, and octamethylcyclotetrasiloxane; cyclic hydrocarbons such as bicyclo[2.2.1]heptane, bicyclo[2.2.2]octane, pinane, dihydrocyclopentadiene, and tetrahydrodicyclopentane diene; and terpene hydrocarbons such as limonene, α-pinene, β-pinene, and dipentene can be given.

The other liquid organic compounds are included in an amount of usually 30 wt % or less, preferably 10 wt % or less, and particularly preferably 5 wt % or less of the total amount of the solvent.

The solvent of the present invention contains water preferably in an amount of 100 ppm or less, with 60 ppm or less being even more preferable, and 30 ppm or less being particularly preferable. If the water content of the solvent exceeds 100 ppm, the reaction may not produce the target yield when the solvent of the present invention is used in a reaction in which an organic metal is used. For example, in the Grignard reaction for producing a Grignard reagent shown by the formula RaMgXa (wherein Ra is an alkyl group and Xa is a halogen atom), the Grignard reagent is not produced at a sufficient yield if water is present in a large amount. Since the Grignard reagent produced easily reacts with water, the Grignard reagent in an amount equivalent to the water remaining in the solvent is consumed by the reaction with the water, thereby lowering the reaction yield.

In one of the methods for reducing the water content of the solvent to 100 ppm or less, the solvent of the present invention prior to drying is caused to come in contact with a dehydrating agent.

As the dehydrating agent, those known in the art that are stable when used in combination with a cycloalkyl alkyl ether compound may be used without any particular limitations. As specific examples of the dehydrating agent, adsorptive porous substances such as molecular sieve (hereinafter abbreviated as "MS"), activated alumina and silica gel, and salts possessing neutral or near neutral absorption properties such as anhydrous magnesium sulfate, anhydrous sodium sulfate, and calcium chloride can be given. Of these, MS, calcium chloride, and anhydrous magnesium sulfate capable of effectively dehydrating in a short period of time are preferable, with MS being particularly preferable.

Tetrahydrofuran (THF) is given as a typical solvent that has been conventionally used with Grignard reactions. According to the investigation of the present inventors, lowering the water content of THF below 250 ppm is difficult when THF is contacted with MS or the like as the dehydrating agent oh an industrial scale. On the other hand, if the solvent of the present invention is caused to come in contact with MS or the like as the dehydrating agent, the water content is easily reduced to 30 ppm or less. Therefore, by using the solvent of the present invention as a reaction solvent in a Grignard reaction or an organic metal reaction, a high reaction yield can be achieved in comparison to using THF.

There are no specific limitations to the method of contacting the solvent of the present invention with the dehydrating agent. For example, a flow-type comprising using a column packed with a dehydrating agent such as MS and causing the solvent of the present invention to passed through the column, or a batch-type comprising placing the solvent of the present invention and the dehydrating agent in a reactor equipped with a stirrer and stirring the mixture to cause the solvent and the dehydrating agent to come into contact can be given. The water content of the solvent of the present invention can be analyzed using Karl-Fischer coulometric titration.

The solvent of the present invention preferably comprises an antioxidant. If the antioxidant is added, the peroxide content of the solvent can be maintained below 100 ppm even if the solvent is stored for a long period of time or repeatedly distilled for recovery. When the solvent of the present invention is used as a cleaning-solvent, the solvent is used for a long period of time at a high temperature of 90° C. or more to achieve an increased cleaning effect or repeatedly distilled for recovery. Adding an antioxidant can prevent an increase in the peroxide content in the cleaning solvent. In other words, a cleaning solvent possessing excellent cleaning effect and stability can be obtained by the combination of at least one type of cycloalkyl alkyl ether compound and an antioxidant.

The amount of the antioxidant can be selected from a wide range depending on the conditions of use. However, from the viewpoint of stability, cleaning power, and cost, the antioxidant is preferably used in an amount of 0.0005-5 wt % of the total amount of the solvent.

As examples of the antioxidant, phenols, aromatic amines, and phosphorous acid esters can be given, with phenols being preferable from the viewpoints of antioxidation effect and cost.

The phenols is an essential component for the solvent of the present invention for preventing deterioration and soiling during processing at a high temperature such as heating, distillation, and recovery. A specific phenol compound is selected from those capable of suppressing production of peroxides without adversely affecting the solvent.

As specific examples of the phenols, 2,6-di-t-butyl-p-cresol, timor, pyrocatechin, 4-methoxyphenol, n-propyl gallate, and 2-t-butylhydroquinone can be given. Of these, 2,6-di-t-butyl-p-cresol is particularly preferable.

The solvent of the present invention may also contain other components in addition to the cycloalkyl alkyl ether compound and the above-mentioned other liquid organic compounds. The other components may be appropriately selected in accordance with the application such as cleaning solvent, reaction solvent, extraction solvent, and electronic and electrical solvent.

(D) Cleaning Solvent

The cycloalkyl alkyl ether compound shown by the above formulas (1), (2), and (3) excels in dissolving a wide range of organic compounds such as machine oil, cutting oil, rosin, waxes, and higher fatty acids. Therefore, the solvent of the present invention is useful as a cleaning solvent for fats and oils, resins, coating materials, lacquers, and varnishes. The cleaning solvent of the present invention comprises the cycloalkyl alkyl ether compound usually in an amount of 70 wt % or more, with 90 wt % or more being preferable, and 95 wt % being even more preferable.

When the solvent of the present invention is used as a cleaning solvent, anionic surfactants, cationic surfactants, ionic surfactants, nonionic surfactants, rust preventive agents, and polishing agents may be added to the solvent as the above-mentioned other additives. The other additives may be added in an amount of usually 0-30 wt % of the total amount of the cleaning solvent.

The cleaning solvent of the present invention is effective for cleaning articles made from metal, ceramic, glass, plastic, elastomer, and fiber in the industries of precision machinery, automobiles, aircrafts, heavy machinery, metal processing, metal assembly, steel, non-iron, steel pipe, heat treatment, plating, metallurgy, optical machines, office machines, electronics, electrics, plastics, glass, ceramics, printing, fibers, and cleaning.

As specific examples of the articles that can be cleaned with the cleaning solvent of the present invention, automotive parts such as bumpers, gears, transmission parts, and radiator parts; electronic and electrical parts used in computers and the peripheral devices, electrical household appliances, communication machines, OA machines, and other electronic application machines such as electric printed wiring substrates, IC parts, lead frames, resistors, relays, hoops used for relay contact points, motor parts, condensers, liquid crystal display machines, magnetic recording parts, semiconductor materials such as silicon wafers and ceramic wafers, parts for electrostriction such as crystal oscillators, opto-electronic transformer parts, brushes, rotors, ticket dispensing parts for vending machines, and currency inspection parts for vending machines and cash dispensers; precision machinery components such as super-hard chips, bearings, gears, gears made of engeneering plastic, watch parts, camera parts, and optical lenses; large machinery parts such as printing machines, printing machine blade, printing rolls, rolling machines, construction machines, and heavy machinery parts; high precision processing products with resin such as cameras and cars; daily life products such as tableware, metal fittings, tools, eyewear frames, and watch belts; textiles (stain remover, removing and cleaning grease on cotton, oil stains, and protein); devices for producing electronic equipment (removal and cleaning of attached resin and oil) such as dry etching apparatus, normal pressure CVD (Chemical Vapor Deposition) devices, reduced pressure CVD devices, dry etching devices, plasma CVD devices, optical CVD devices, plasma etching devices, and RIE (Reactive Ion Etching) devices; and the like can be given.

There are no specific limitations to the pollutants that can be cleaned with the cleaning solvent of the present invention. For example, oils such as cutting oils, water soluble cutting oils, quenching oils, heat treatment oils, rolling oils, stretching oils, lubricating oils, rust prevention oils, forging oils, machine oils, handicraft oils, processing oils, press processing oils, punching oils, pattern cutout oils, drawing oils, assembling oils, line pulling oils, oils containing extreme pressure additives, and synthetic oils (silicon, glycol, and ester types); greases, waxes, paint, inks, rubber, varnishes, coating materials, polishing agents, adhesives, adhesive solvents, surface delaminating materials, fats and oils, parting agents used during molding, asphalt pitch, dirt from the print, fingerprints, proteins, flux after soldering, resists, antireflection films for resists, coatings for optical lenses, OPC (Organic Photo Conductor) drum photosensitizers, photosensitive resins (photosensitive resists), masking agents, compounds, surface active agents, solder paste, cutting scraps, cutting powder, lens pitch (lens polishing agents), metallic powder, metallic polishing agents, lubricants, resins (melamine resins, polyurethanes, polyesters, epoxy resins, and rosin), processing waste, burrs, resin powders, non-organic powders, paper powders, puff powders, particles, ionic stains, dust, and water can be given.

Favorable results can be achieved when the cleaning solvent of the present invention is used in various cleaning methods such as immersion, ultrasonic cleaning, agitation, spraying, showering, vapor cleaning, and wiping. Physical means such as stirring, agitation, and brushing may be employed during use of the cleaning solvent when necessary.

(E) Reaction Solvent

The cycloalkyl alkyl ether compounds of the above formulas (1), (2), or (3) exhibit excellent solubility to a variety of chemicals and ionic substances and are chemically stable with various reactive substances in a wide temperature range. Therefore, the solvent of the present invention may be used as a reaction solvent in various types of reactions.

The reaction solvent of the present invention comprises the cycloalkyl alkyl ether compound usually in an amount of 30 wt % or more, and preferably 50 wt % or more.

When the solvent of the present invention is used as a reaction solvent, aliphatic hydrocarbons, aromatic hydrocarbons, alicyclic hydrocarbons, ethers, nitriles, and amides, for example, may be added to the solvent as the above-mentioned liquid organic compounds. The other liquid organic compounds are included in an amount of usually 30 wt % or less, preferably 10 wt % or less, and particularly preferably 5 wt % or less of the total amount of the solvent.

There are no specific limitations to the type of reaction in which the reaction solvent of the present invention is used. Since the reaction solvent of the present invention comprises a cycloalkyl alkyl ether compound, which is one type of ether compound, it is preferably used as a reaction solvent in the reaction using other types of ether solvents such as diethyl ether and tetrahydrofuran.

As examples of such a reaction, various polymerization reactions such as anionic polymerization, cationic polymerization, and radical polymerization, (co)oligomerization, oxidation reaction, reduction reaction, nucleophilic displacement reaction, electrophilic displacement reaction, rearrangement reaction, addition reaction, elimination reaction, addition elimination reaction, insertion reaction, isomerization, decomposition reaction, solvolysis reaction, coupling reaction, metathesis reaction, carbene reaction, condensation reaction, asymmetric synthesis reaction, pericyclic reaction, photochemical reaction, electrochemical reaction, radical reaction, ring-opening reaction, cyclization reaction, cleavage reaction, hydrogenation reaction, esterification reaction, halogenation reaction, carbonylation reaction, heterocycle synthesis reaction, dehydration reaction, hydration reaction, reaction using a transition element or an organic metal of typical element, chemical reaction using a metal catalyst (metal complex), and reaction using a rare earth element can be given.

Of these reactions, the solvent of the present invention is preferably used as a reaction solvent in the reactions in which a Grignard reagent, organiolithium, lithium amide, alkali metal or alkaline earth metal, metal hydride, alkali metal hydroxide, alkaline earth metal hydroxide, alkali metal carbonate, alkaline earth metal carbonate, alkali metal hydrogencarbonate, alkaline earth metal hydrogencarbonate, metal alkoxide, an organic base such as pyridine, triethylamine, organometalic compound such as organoaluminum compound, organotin compund is used.

In particularly, the solvent of the present invention is preferably used in the reactions in which Grignard reagents such as methyl magnesium bromide, methyl magnesium iodide, ethyl magnesium bromide, ethyl magnesium iodide, isopropyl magnesium bromide, cyclopentyl magnesium bromide, cyclohexyl magnesium bromide, phenyl magnesium bromide, phenyl magnesium iodide, 2,4,6-trimethylphenyl magnesium bromide, and 2,4,6-trimethylphenyl magnesium iodide; organolithiums such as methyl lithium, n-butyl lithium, sec-butyl lithium, tert-butyl lithium, and phenyl lithium; lithium amides such as lithium diisopropylamide and lithium hexamethyl disilazide; metal hydrides such as lithium hydride, sodium hydride, calcium hydride, lithium aluminum hydride, and diisobutyl aluminum hydride; and the like are used as a nucleophile agent.

The reaction solvent of the present invention is particularly useful in the reaction of producing a secondary alcohol of the formula $(Rb)(Rc)CHOH$ by reacting a Grignard reagent of the formula $RbMgXb$ with an aldehyde of the formula $RcCHO$ and the reaction of producing a tertiary alcohol of the formula $(Rb)(Rd)(Re)COH$ by reacting a Grignard reagent of the formula $RbMgXb$ with a ketone of the formula $RdReC(=O)$, wherein Rb, Rc, Rd, and Re individually represent a hydrocarbon group provided that Rd and Re may form a carbon ring with 3-8 carbon atoms in combination, wherein the carbon ring may contain a hetero atom such as a sulfur atom or nitrogen atom.

As examples of the hydrocarbon group, an alkyl group; alkenyl group, alkynyl group, and aryl group can be given. There are no specific limitations to the number of carbon atoms possessed by the hydrocarbon group. The hydrocarbon group usually possesses 1-30 carbon atoms, and preferably 1-20 carbon atoms. As examples of the alkyl group, a linear alkyl group such as a methyl group, ethyl group, n-propyl group, isopropyl group, n-butyl group, isobutyl group, sec-butyl group, tert-butyl group, n-pentyl group, neopentyl group, isopentyl group, n-hexyl group, n-heptyl group, n-octyl group, and n-decyl group, and a cycloalkyl group such as a cyclopropyl group, cyclobutyl group, cyclopentyl group, cyclohexyl group, cycloheptyl group, and cyclooctyl group can be given. As examples of the alkenyl group, a vinyl group, 1-propenyl group, 2-propenyl group, 1-butenyl group, 2-butenyl group, 3-butenyl group, butadienyl group, 1-pentenyl group, 2-pentenyl group, 3-pentenyl group, 4-pentenyl group, 1,3-pentadienyl group, and 2,4-pentadienyl group can be given. As examples of the alkynyl group, an ethynyl group, propargyl group, and 2-butynyl group can be given. As examples of the aryl group, a phenyl group, 2-pyridyl group, 3-pyridyl group, 4-pyridyl group, 5-pyridyl group, 2-furyl group, 3-furyl group, 2-thienyl group, 3-thienyl group, 1-naphthyl group, and 2-naphthyl group can be given.

These hydrocarbon groups may possess substituents such as a nitro group, alkyl group, alkoxy group, alkylthio group, alkylsulfonyl group, dialkylamino group, dialkyl sulfamoyl group, and dialkyl phosphoryl group attached to any position. When these hydrocarbon groups possess more than one substituent, the substituents may be the same or different.

Xb represents a halogen atom such as a chlorine atom, bromine atom, or iodine atom. Although there are no specific limitations to the amount of the reaction solvent used in the present invention, the reaction solvent is usually used in an amount of 0.001-1,000 parts by weight, and preferably 0.01-100 parts by weight, for one part by weight of the total amount of the reaction materials. The reaction using the reaction solvent of the present invention is usually conducted at a reaction temperature from $-100°$ C. to the boiling point of the solvent.

The reaction solvent of the present invention excels in reaction selectivity. For example, if a Grignard reagent is reacted with a ketone that can be easily enolized using other ether solvent such as THF, a self-aldol reaction predominates. However, the target alcohol can be obtained in a high yield by using the reaction solvent of the present invention.

The cycloalkyl alkyl ether compound possesses a very low miscibility with water. Even though this compound produces an azeotrope with water, the compound can be easily separated from the water. Therefore, after conducting the reaction using the reaction solvent of the present invention, the reaction solvent can be conveniently and efficiently recovered from the reaction mixture. The target reaction solvent can be easily isolated from the reaction mixture, for example, by adding water (or an aqueous acid solution) to the reaction mixture using the reaction solvent of the present invention to terminate the reaction, separating the reaction mixture into a water layer and an organic layer, removing the reaction solvent from the organic layer, and purifying the residue using a known method such as distillation and column chromatography.

Furthermore, since the reaction solvent of the present invention has a moderate boiling point, the reaction solvent can be efficiently recovered from the reaction mixture. The recovered reaction solvent is purified, as required, and can be reused as a reaction solvent.

(F) Extraction Solvent

The cycloalkyl alkyl ether compounds of the above formulas (1), (2), or (3) exhibit excellent solubility to a variety of chemicals and are chemically stable with various reactive substances. Therefore, the solvent of the present invention is also useful as an extraction solvent for extracting organic compounds from a solid or liquid mixture containing the organic compounds.

The content of the cycloalkyl alkyl ether compound in the extraction solvent of the present invention is usually 70 wt % or more, preferably 90 wt % or more, and still more preferably 95 wt % or more.

There are no specific limitations to the extracted organic compounds inasmuch as such compounds can be dissolved in the cycloalkyl alkyl ether compound. From the view point that the extraction solvent of the present invention functions as a substitute for conventional extraction-solvents, organic compounds exhibiting excellent solubility in conventional extraction solvents such as aliphatic halogenated hydrocarbons, esters, and aromatic hydrocarbons are preferable.

Organic compounds having a polar group in the molecule can be given as such organic compounds. The polar group here indicates a group containing atoms having electronegativity different from that of the carbon atom such as an oxygen atom, nitrogen atom, and sulfur atom. As examples of the polar group, an amide group, carboxyl group, ester group, hydroxyl group, carbonyl group, amino group, nitro group, cyano group, alkoxy group, mercapto group, and alkylthio group can be given.

As examples of the organic compound having a polar group in the molecule, naturally occurring substances, active ingredients of medical supplies and agricultural chemicals, industrial chemicals, perfumes, intermediates for manufacturing these substances, and the like having one or more polar groups in the molecule can be given. Although there are no specific limitations, the molecular weight of these organic compounds is usually 100-500, and preferably 100-300.

In the case where the organic compound to be extracted has an asymmetrical carbon atom in the molecule, such an organic compound may be either a mixture of optical isomers or one of the optical isomers. No racemization reaction occurs during the extraction operation.

As a method of solvent extraction, liquid-liquid extraction for extracting an organic compound from a solution that comprises adding an extraction solvent immiscible with the solvent of the organic compound solution to cause the organic compound to move to the extraction solvent by utilization of the difference in the distribution coefficient, solid-liquid extraction that comprises adding the extraction solvent to a solid mixture containing the organic compound to cause the organic compound to be extracted in the solvent, and the like can be given. The extraction solvent of the present invention is particularly useful for extracting an organic compound from an aqueous solution of the organic compound, since the extraction solvent dissolves with water only very slightly and can be easily separated from water.

More specifically, the liquid-liquid extraction includes (i) a method of adding the extraction solvent of the present invention to an aqueous solution of an organic compound of which the solubility in the extraction solvent is higher than that in water, sufficiently shaking the mixture, allowing the mixture to stand still to be separated into a water layer and an organic layer, and to remove the organic layer, (ii) a method for extracting a salt of an acidic organic compound such as carboxylic acid or a salt of a basic organic compound from an aqueous solution comprising adding an acid (in the case of the salt of an acidic compound) to liberate the acidic compound or a base (in the case of the salt of a basic compound) to liberate the basic compound and extracting the liberated acidic organic compound or basic organic compound using the extraction solvent of the present invention, and the like. In this instance, the extraction operation can be repeated several times. The extraction temperature is usually −20 to 100° C., preferably 0-90° C., and still more preferably 20-50° C.

The liquid-liquid extraction is carried out using a separating funnel in experiments in laboratories. When a large quantity of materials are processed, a known-separating apparatus (a mixer settler), a multiple mixer decanter type contactor, a gravity fractionation column type contactor, and the like can be used.

When a separating funnel is used, an appropriate amount of the extraction solvent of the present invention is added to the aqueous solution containing the target compound to be extracted and the mixture is sufficiently shaken. Then, the mixture is allowed to stand to completely separate into two layers, an organic layer and a water layer, and the organic layer is removed.

A known separating apparatus (mixer settler), which is a large scale separating funnel, can be operated according to the method of operating an experimental-scale separating funnel.

The multiple mixer decanter type contactor is a non-agitating type extractor that is typically operated by charging a light liquid with a small specific gravity (the extraction solvent of the present invention) from the bottom of the extractor and a heavy liquid with a large specific gravity (an aqueous solution, etc.) from the top. Since the light liquid flows upwardly and the heavy liquid flows downwardly in the apparatus, the two liquids contact in the column. The components dissolved in the light liquid and the heavy liquid are distributed to each liquid layer according to the distribution coefficient. In this instance, if multi stage porous plates are installed in the extraction column, the light liquid ascends the column as droplets through pores in the porous plates and the drops come into contact with the heavy liquid. A large number of droplets further ascend the column through pores in the porous plates. The two liquids efficiently contact each other by repeating the formation and association of droplets in this manner.

The gravity fractionation column type contactor is an extractor in which stirring is mechanically performed. As the method for stirring, a method of using stirring blades, a method of vibrating by pulse, and the like can be given.

As a specific example of the solid-liquid extraction, a method of sufficiently mixing the solid containing the organic compound to be extracted with the extraction solvent of the present invention, extracting the target organic compound, and removing insoluble matters by filtration or the like can be given. The solid mixture may be finely pulverized before extraction to increase the extraction efficiency. The extraction solvent may be heated during the extraction.

As the extraction apparatus used for the solid-liquid extraction, known extractors such as an extractor of the type having a cloth filter or a porous plate installed in the bottom can be used. The solid containing the organic compound to be extracted is placed on the cloth filter or porous plate and the extraction solvent is circulated through the extractor. When a large quantity of materials is processed by solid-liquid extraction, a continuous extractor described in Published Japanese Translation of PCT Application 9-510913, for example, can be used.

In any apparatus, the extraction solvent phase is removed and dried, as required, following which the extraction solvent is evaporated. The resulting residue is purified by a known purification means such as washing with a solvent, recrystallization, column chromatography, and distillation to isolate the target product. When the extract is a thermally unstable compound such as a natural product, a means such as a method of removing extraction solvent under reduced pressure, a method of decreasing partial pressure of the solvent by injecting steam (steam stripping), or the like is necessary.

The extraction solvent used for the extraction is recovered by a solvent recovery apparatus, purified by distillation or the like, as required, and again used as the extraction solvent.

(G) Solvent for Electronic and Electrical Materials

The cycloalkyl alkyl ether compounds of the above formulas (1), (2), or (3) can exhibit excellent solubility to electronic and electrical materials, exhibit only slight toxicity, and are almost free from the problem of environmental pollution. Therefore, the solvent of the present invention is also useful as a solvent for electronic and electrical materials.

When the solvent of the present invention is used as a solvent for electronic and electrical materials, other liquid organic compounds such as alcohol solvents, ether solvents, ketone solvents, ester solvents, amide solvents, aliphatic hydrocarbons, and aromatic hydrocarbons may be added.

The electronic and electrical materials indicate materials used for manufacturing information recording media, OA machines, communication machines, electronic equipment, electronic parts, electrical products, and the like. Specific examples that can be given include a material for forming a recording layer of information recording media, a material for forming a photosensitive layer of OA equipment and communication machines, a material for forming insulating layer used in OA equipment, communication machines, electronic equipment, electronic parts, and electrical appliances, and a raw material for manufacturing separator porous membranes of battery cells.

Coloring matters conventionally known as recording materials for information recording media can be used as the material for forming recording layers (hereinafter referred to as "recording material"). As examples of the coloring matter, cyanine dyes, phthalocyanine dyes, pyrylium dyes, thiopyrylium dyes, azulenium dyes, squalelium dyes, metal complex salts of Ni, Cr, or other metals, naphthoquinone dyes, anthraquinone dyes, indophenol dyes, indoaniline dyes, triphenylmethane dyes, triallylmethane dyes, aluminum dyes, diimmonium dyes, and nitroso compound dyes can be given.

The recording layer can be formed by coating a coating solution for forming a recording layer onto a substrate and drying the coating. As the substrate, a synthetic resin substrate such as a methyl methacrylate resin substrate, vinyl chloride resin substrate, epoxy resin substrate, and polycarbonate resin substrate; a glass substrate such as a soda lime glass substrate; ceramics substrate; and the like can be given. A substrate provided with a primer coating layer and/or a pre-groove layer on the surface of the side on which the recording layer is provided can be used.

The primer coating layer is formed to improve the surface properties, increase adhesiveness, and prevent denaturing of the recording layer. As materials for the primer coating layer, polymers such as polymethylmethacrylate, acrylic acid-methacrylic acid copolymer, polyvinyl alcohol, N-methylolacrylamide, styrene-sulfonic acid copolymer, styrene-vinyltoluene copolymer, chlorosulfonated polyethylene, nitro cellulose, polyvinyl chloride, chlorinated polyolefin, polyester, polyimide, vinyl acetate-vinyl chloride copolymer, ethylene-vinyl acetate copolymer, polyethylene, polypropylene, and polycarbonate; organic materials such as silane coupling agent; inorganic materials such as inorganic oxide ($SiO_2$, $Al_2O_3$, etc.) and fluorinated inorganic compounds ($MgF_2$, etc.); and the like can be given. The thickness of the primer coating layer is usually 0.005-20 μm, and preferably 0.01-10 μm.

The pre-groove layer is provided to form tracking grooves or irregularities expressing information such as address signals. As materials for the pre-groove layer, a curing agent obtained from a mixture of at least one monomer (or oligomer) selected from the group consisting of monoester, diester, triester, and tetra ester of acrylic acid and a photoinitiator can be given. The thickness of the pre-groove layer is usually 0.05-50 μm, and preferably 0.1-20 μm.

In addition to the above-described coloring matters; the coating solution for forming recording layer may include naturally occurring organic polymers such as gelatin, cellulose derivatives, dextran, rosin, and natural rubber and synthesis organic polymers such as polystyrene, polyisobutylene, polyvinylidene chloride to increase spreadability of the coloring matter on substrates, as well as binders, antioxidants, UV absorbents, plasticizers, lubricants and the like.

The coating solution for forming recording layer can be prepared by dissolving or dispersing the coloring matter and other optional components such as binders, antioxidants, UV absorbents, plasticizers, and lubricants in the solvent of the present invention. The content of solid components such as coloring matters and binders in the solution of the coating solution for forming recording layer is usually 0.1-30 wt %, and preferably 0.2-20 wt %.

The recording layer can be formed by coating the coating solution onto a substrate and drying the coating. As a method of applying the coating composition to the substrates, a spin coating method, spray method, dip method, roll coating method, blade coating method, doctor roll method, screen printing method, and the like can be given. The recording layer may be either a single layer or multiple layers, with a thickness of usually 0.01-10 µm, and preferably 0.02-1 µm. The recording layer may be formed either on one side or on both sides of the substrate.

In addition, a reflecting layer made from a metal such as Al, Cr, or Ni exhibiting a high reflectance to laser beams may be formed on the recording layer to increase the S/N ratio during reproduction of information and to promote sensitivity during recording. The thickness of the reflecting layer is usually 10-300 nm. A protective layer may be formed on the recording layer or the reflecting layer to increase scratch resistance and moisture resistance. The thickness of the protective layer is usually 0.1-100 µm.

The photosensitive layer can be formed by preparing a coating solution for forming a photosensitive layer by dissolving or dispersing at least one photoconductive substance in the solvent of the present invention and applying the solution to a supporting substrate for the photoconductive substance and drying the coating. The photosensitive layer may also be formed from a combination of a charge generating layer and a charge transport layer. For example, the charge generating layer can be formed by preparing a coating solution for forming a charge generating layer by dissolving or dispersing a charge generating material in an appropriate solvent, applying the solution to a supporting substrate for the photoconductive substance and drying the coating. The charge transport layer can be formed by preparing a coating solution for forming a charge transport layer by dissolving or dispersing a charge transport material in the solvent of the present invention and applying the solution to the surface of the charge generating layer and drying the coating.

As examples of the conductive supporting material, conductive supporting materials in which the supporting materials themselves are conductive, such as aluminum, aluminum alloy, stainless steel, chromium, and titanium; conductive supporting materials composed of an insulating substrate such as a formed synthetic resin and a coating of aluminum, aluminum alloy, or indium-tin oxide alloy formed thereon by vacuum vapor deposition or the like; and conductive supporting materials produced by impregnating plastic or paper with carbon black or tin oxide particles together with an appropriate binder. A drum for an OPC drum can be given as a particularly preferable example of the conductive supporting material.

As examples of the photoconductive material, organic photoconductive polymers such as poly-N-vinylcarbazole and polyvinyl anthracene; low molecular weight organic photoconductive compounds such as carbazole, anthracene, pyrazolines, oxadiazoles, hydrazones, and polyacetal alkanes; and inorganic photoconductive materials such as amorphous silicon and selenium can be given. As examples of the charge generating materials, one or more types of azo pigments, quinone pigments, quinocyanine pigments, perylene pigments, indigo pigments, bisbenzimidazole pigments, phthalocyanine pigments, and quinacdorine pigments can be given. As examples of the charge transfer materials, hydrazone compounds, stilbene compounds, pyrazoline compounds, oxazole compounds, thiazole compounds, and triaryl methane compounds can be given.

A binder may optionally be added to the coating solution for forming photosensitive layer, coating solution for forming charge generating layer, and the coating solution for forming charge transport layer. As the binder that can be added, insulating resins such as polyvinyl butyral, polyallylate, polycarbonate, polyester, phenoxy resin, acrylic resin, polyacrylamide, polyamide, cellulose resin, urethane resin, epoxy resin, casein, and polyvinyl alcohol; organic photoconductive polymers such as carbazole, polyvinyl anthracene, and polyvinyl pyrene; and the like can be given.

Although not specifically limited, the content of solid components in the above coating solution for forming photosensitive layer, coating solution for forming charge generating layer, and the coating solution for forming charge transport layer is usually 1-90 wt %, and preferably 10-80 wt %.

The thickness of the photosensitive layer formed is usually in the range of 5-200 µm, and preferably 5-100 µm, and the thickness of the charge generating layer formed is usually in the range of 0.01-20 µm, and preferably 0.01-15 µm. The thickness of the charge transport layer is usually 3-100 µm, and preferably 5-50 µm.

It is possible to use a drum for an OPC drum as the conductive supporting material. When a photosensitive layer is formed on the drum, it is possible to form an under layer having both the barrier function and the attaching function between the drum and the photosensitive layer. The under layer can be formed from casein, polyvinyl alcohol, nitro cellulose, ethylene-acrylic acid copolymer, polyamide, polyurethane, gelatin, aluminium oxide, and the like. The thickness of the under layer is preferably 5 µm or less, and more preferably 0.5-3 µm.

The porous membrane for the cell separator is provided between the positive electrode active material and the negative pole active material in the cell to prevent a short circuit. In the case of a closed-type cell, the porous membrane also has a function of holding the electrolyte. Such a porous membrane can be formed using a solution of resin dissolved in the solvent of the present invention by a uniaxial or biaxial drawing. Polypropylene, polyethylene, and the like are used as the resin. A porous membrane with a multilayer structure such as a monolayer structure or two or more layer structure can be formed from a resin solution in which one or more types of these resins are dissolved.

An electric insulating layer for OA equipment, communication equipment, electronic equipment, electronic parts, electric appliances, and the like can be formed using a resin solution prepared by dissolving or dispersing an organic insulating material in the solvent of the present invention. Polyurethane, epoxy resin, polyethylene terephthalate, polyester imide, heat resistant polyester, polyimide, polyamideimide, and norbornene-type resin can be given as examples of the organic insulating material to be used with the solvent of the present invention.

As examples of the method for forming an electric insulating layer, a method of applying the resin solution prepared by dissolving or dispersing an organic insulating material in the solvent of the present invention to a substrate and drying the resulting coating, a method of forming films or sheets of insulating resin from a resin solution prepared by dissolving or dispersing an organic insulating material in the solvent of the present invention and laminating the films or sheets can be given. There are no specific limitations to the substrate inasmuch as the material is an intermediate for fabricating OA equipment, communication equipment, electronic equipment, electronic parts, electric appliances, and the like and can be provided with an insulating layer thereon.

(H) Parting Agent

The cycloalkyl alkyl ether compounds of the above formulas (1), (2), or (3) can exhibit excellent solubility to photosensitizers, organic adhesives, photosensitive resists, and organic insulating materials, exhibit only slight toxicity, and are almost free from the problem of environmental pollution. Therefore, the solvent of the present invention is also useful as a parting agent. Specific examples include (a) a parting agent for removing a photosensitive layer from a photosensitive drum and (b) a parting agent that can be used for removing adhesive parts from jigs for fabrication in the case when semiconductor materials, crystal materials, electronic part materials, magnetic materials, piezo materials, and the like (hereinafter referred to as "adhered materials") are caused to adhere to jigs and are processed by cutting, grinding, or the like.

In the case of manufacturing OPC drums by forming a photosensitive layer on a photosensitive drum, if the thickness of the photosensitive layer is not uniform, defective goods with an impaired image are produced due to uneven charge conditions. For this reason, the photosensitive layer must be removed from the drum and a new photosensitive layer must be formed. In this instance (in the case of (a)), the photosensitive layer can be easily parted from the drum by dipping the defective OPC drum in the solvent of the present invention and removing it therefrom.

In the case of (b), the adhered materials attached to the jigs using an organic adhesive can be easily parted by dipping the adhered materials in the solvent of the present invention and then removing therefrom. In the above cases (a) and (b), the drums and materials may be heated or treated with supersonic waves to promote the effect of parting.

As examples of the semiconductor material, silicon, gallium-arsenic, and gallium-phosphorus can be given. Crystal materials, rock crystals, quartz, and glass can be given as examples of crystal and electronic part-related materials. As the magnetic material, ferrite, samarium, cobalt and the like can be given. As the magnetic material and piezo material, magnetic heads and the like can be given.

As examples of the organic adhesive, synthetic resin adhesives such as epoxy resin adhesive and polyurethane adhesive; elastomer-type adhesives such as chloroprene rubber adhesive, acrylonitrile-butadiene rubber adhesive, styrene-butadiene rubber adhesive, and thermoplastic elastomer adhesives (adhesives containing styrene-butadiene block copolymer elastomer, styrene-isoprene block copolymer elastomer, or styrene-ethylene-butylene block copolymer elastomer as main components); mixed adhesives such as a mixed adhesive of vinyl resin and phenol resin, mixed adhesive of nitrile rubber and phenol resin, and mixed adhesive of chloroprene rubber and phenol resin, mixed adhesive of epoxy resin and phenol resin, and a mixed adhesive of epoxy resin and soluble nylon can be given.

The parting agent of the present invention is particular preferable for removing epoxy resin adhesive among these adhesives. The epoxy resin adhesive comprises an epoxy resin and a curing agent as essential components and optionally contains additives such as fillers and denaturing agents.

As the main component epoxy resin, glycidyl ether-type epoxy resins such as bisphenol A-based epoxy resin, novolak-based epoxy resin, and bisphenol F-based epoxy resin; alicyclic epoxy resin, glycidyl ester-type epoxy resin, glycidyl amine-type epoxy resin, hydantoin-type epoxy resin, heterocyclic epoxy resin such as triglycidyl isocyanurate, low viscosity epoxy resin, and the like can be given.

As examples of the curing agent, curing agents of primary amine such as aliphatic amine, alicyclic amine and aromatic amine, room-temperature curing-type such as secondary amine, tertiary amine, polyamide, imidazole, acid anhydride, and mercaptan-type curing agents; potential curing type such as dicyandiamide, organic acid hydrazide, and Lewis acid amine complex curing agents can be given.

As the type of epoxy resin adhesives, two-solution type room temperature setting adhesives, one-solution potential curing type paste adhesives, one-solution potential curing type film adhesives, one-solution curing type powdery adhesives, and the like can be given. The solvent of the present invention can be used as parting agent for any types of adhesive.

The epoxy resin adhesives are used, for example, for adhering a semiconductor ingot of silicon or the like fabricated to have a prescribed outside configuration to a slice space of carbon or the like. The adhered material is cut into wafers or plates using a slicing machine (slicer) of inner circle edge-type, band saw-type, or wire saw-type. After removing the slice space and epoxy resin adhesive, the wafers or plates are sent to the next steps for annealing, wrapping, and the like. The solvent agent of the present invention is particular preferably used as the parting agent for removing the slice space and the epoxy resin adhesive from the wafers.

The solvent of the present invention can also be used as a solvent for crystallization or recrystallization, raw material for lacquers, solvent for regenerating reclaimed rubber, solvent for extracting wax and resins, octane booster for gasoline, antiknock agent, miscibility improver for lacquers, dispersant for organosol, dying stabilizer, electrolyte for lithium cell or the like, particle removing agent, cleaning solution, plasticizer, lubricant, humectant, solvent for gel permeation chromatography (GPC), solvent for high performance liquid chromatography (HPLC), solvent for column chromatography, dissolution agent for polymer and the like, casting solvent, primer for adhesives, solvent for spin coat, and the like.

EXAMPLES

The present invention will be described in more detail by way of examples and comparative examples. The present invention, however, should not be limited to these examples. In the examples and comparative examples below "parts" indicates "parts by weight", unless otherwise specified.

The following conditions were applied to analysis by gas chromatography, unless otherwise indicated.

Analytical apparatus: Hitachi GC390

Column: Neutrabond Capillary Column 60×ID 0.25φ(1.5 µm df manufactured by GL Science Inc.)

Column temperature: 50° C. (10 minutes) 100° C.->300° C. (20° C./min)

Temperature at the inlet port: 200° C.

Detector temperature: 300° C.

Carrier gas: $N_2$

Detector: FID

Injection amount: 0.1 µl

PREPARATION EXAMPLE 1 Preparation of Cyclopentyl Methyl Ether

A 1 little four-necked flask was charged with 283 parts of N,N-dimethylformamide. After replacing the internal atmosphere with nitrogen, 58.0 parts of 60 wt % oily sodium hydride was added. Then, 103.3 parts of cyclopentanol was added dropwise at a temperature between room temperature and 50° C. The mixture was heated to 110° C. in one hour and refluxed at 110-120° C. for one hour. After cooling the mixture to 50° C., 341.0 parts of methyl iodide was added dropwise. After the addition, the mixture was refluxed at 110-120° C. for five hours.

After evaporating low boiling point components from the reaction mixture, 100 parts of water was added to partition the mixture into two layers. The organic layer was dried over anhydrous magnesium sulfate and filtered to obtain about 210 parts of a filtrate. The filtrate was rectified using a Vigreux rectification column under atmospheric pressure. 77.1 parts of fraction 1 (Fr. 1) with a distillation temperature up to 100° C., 3.40 parts of fraction 2 (Fr. 2) with a distillation temperature of above 100° C. and below 106° C., 70.0 parts of fraction 3 (Fr. 3) with a distillation temperature of 106° C., and 53.5 parts of tank bottom were obtained. The yields and the results of gas chromatography analysis of these fractions (Fr. 1, Fr. 2, Fr. 3, and tank bottom) are shown in Table 1.

TABLE 1

| Fraction (distillation temperature) | Yield (parts) | Results of gas chromatography analysis (%) |
|---|---|---|
| Fr. 1 (Up to 100° C.) | 77.1 | Methyl iodide (88.3), CPME (3.3) |
| Fr. 2 (100-106° C.) | 3.40 | Methyl iodide (58.7), CPME (40.9) |
| Fr. 3 (106° C.) | 70.0 | CPME (99.8) |
| Tank bottom (more than 106° C.) | 53.5 | CPME (64.4), CPL (19.6) |

CPME: Cyclopentyl methyl ether,
CPL: Cyclopentanol

EXAMPLE 1 Oil and Fat Solubility Test

Solubility of oils and fats (oil, rosin, wax, and fatty acids) shown in Table 2 in CPME obtained in Preparation Example 1 as a cleaning solvent was examined. 1 g (in the case of oil) or 0.5 g (in the case of rosin, wax, and fatty acid) of the sample was added dropwise to a test tube containing 5 ml of CPME to observe the solubility by the naked eye. The results of observation are summarized in Table 2.

TABLE 2

| Oils and fats | Example 1 |
|---|---|
| Press oil No. 660 (Nihon Kohsakuyu Co., Ltd.) | Rapidly dissolved |
| Cutting oil (Magplus LA-15, Idemitsu Kosan Co. Ltd.) | Rapidly dissolved |
| Rosin | Rapidly dissolved |
| Skywax 415 | Dissolved in 20 minutes at 50° C. |
| Stearic acid | Gradually dissolved at room temperature |
| Lauric acid | Rapidly dissolved |
| Docosanic acid | Dissolved in 20 minutes at 50° C. |

COMPARATIVE EXAMPLES 1 And 2 Oil and Fat Solubility Test 1 g (in the case of oil) or 0.5 g (in the case of rosin, wax, and fatty acid) of the sample was added dropwise to a test tube containing 5 ml of NS-100 (a hydrocarbon cleaning solvent manufactured by NIKKO PETROCHEMICALS CO., Ltd.) and a test tube containing 5 ml of t-butyl methyl-ether (a component for cleaning solvent described in Japanese Patent Application Laid-open No. 6-49495) to observed the solubility by the naked eye. The results of observation are summarized in Table 3.

TABLE 3

| Oils and fats | Comparative Example 1 | Comparative Example 2 |
|---|---|---|
| Press oil No. 660 (Nihon Kohsakuyu Co., Ltd.) | Rapidly dissolved | Rapidly dissolved |
| Cutting oil (Magplus LA-15, Idemitsu Kosan Co. Ltd.) | Rapidly dissolved | Rapidly dissolved |
| Rosin | Clouded by stirring | Rapidly dissolved |
| Skywax 415 | Remained turbid when heated | Dissolved in 80 minutes at 50° C. |
| Stearic acid | Dissolved in 40 minutes at 50° C. | Partly dissolved at room temperature and completely dissolved with heating |
| Lauric acid | Partly dissolved at room temperature and completely dissolved with heating | Rapidly dissolved |
| Docosanoic acid | Dissolved in 60 minutes at 50° C. | Dissolved in 30 minutes at 50° C. |

It can be seen from Tables 2 and 3 that the cleaning solvent of Example 1 exhibits far more excellent solubility than NS-100 of Comparative Example 1 and equivalent to or better than t-butyl methyl ether of Comparative Example 2. The cleaning solvent of the present invention has thus been proven to be useful as a solvent for cleaning articles stained with oils and fats.

EXAMPLE 2 Preparation of α, α-dimethylbenzyl Alcohol Using CPME as a Reaction Solvent 45 ml (0.045 mol) of a 1 M phenylmagnesium bromide (PhMgBr) solution in THF was added to a flask, of which the atmosphere had been replaced with nitrogen, and stirred at 0° C. for 30 minutes. A solution of 1.74 g (0.03 mol) of acetone in 50 ml of CPME was slowly added dropwise to the PhMgBr solution at 0° C. After stirring at 0° C. for one hour, the reacted mixture was heated to 50° C. and stirred for a further one hour. The reaction mixture was allowed to cool to room temperature and 20 ml of 1 N hydrochloric acid aqueous solution was added to terminate the reaction. The reaction mixture was analyzed by gas chromatography to confirm that the target α,α-dimethylbenzyl alcohol was obtained in a yield of 70%.

EXAMPLE 3 Preparation of 1-hydroxy-1-phenylcyclopentane and Phenylcyclopentene Using CPME as a Reaction Solvent The same experiment as in Example 2 was carried out, except for using 2.5 g (0.03 mol) cyclopentanone instead of 1.74 g of acetone. The resulting reaction mixture was analyzed by gas chromatography to confirm that the target 1-hydroxy-1-phenylcyclopentane and phenylcyclopentene were obtained in a yield of 90% in total.

EXAMPLE 4 Preparation of 2-mesityl-2-propanol and α-methyl-2,4,6-trimethylstyrene Using CPME as a Reaction Solvent The same experiment as in Example 2 was carried out, except for using 45 ml (0.045 mol) of a 1 M 2,4,6-trimethylphenylmagnesium bromide solution in CPME instead of 45 ml of the 1 M phenylmagnesium bromide solution in THF. The resulting reaction mixture was analyzed by gas chromatography to confirm that 2-mesityl-2-propanol and α-methyl-2,4,6-trimethylstyrene were obtained in a yield of 81.9% and 1.6%, respectively.

EXAMPLE 5 Preparation of 2-mesityl-2-propanol and α-methyl-2,4,6-trimethylstyrene Using CPME-THF Mixture as a Reaction Solvent The same experiment as in Example 4 was carried out, except for using a mixed solvent of CPME and THF (1:1 by volume) instead of 50 ml of CPME. The resulting reaction mixture was analyzed by gas chromatography to confirm that 2-mesityl-2-propanol and α-methyl-2,4,6-trimethylstyrene were obtained in a yield of 66.8% and 14.7%, respectively.

COMPARATIVE EXAMPLE 3 Synthesis of α,α-dimethylbenzyl Alcohol Using THF as a Reaction Solvent The same experiment as in Example 2 was carried out, except for using 50 ml of THF instead of 50 ml of CPME. The resulting reaction mixture was analyzed by gas chromatography to confirm that the yield of the target compound was only 40%.

COMPARATIVE EXAMPLE 4 Preparation of 1-hydroxy-1-phenylcyclopentane and Phenylcyclopentene Using THF as a Reaction Solvent The same experiment as in Example 3 was carried out, except for using 50 ml of THF instead of 50 ml of CPME. The resulting reaction mixture was analyzed by gas chromatography to confirm that the target 1-hydroxy-1-phenylcyclopentane and phenylcyclopentene were obtained in a yield of 85% in total.

COMPARATIVE EXAMPLE 5 Preparation of 2-mesityl-2-propanol and α-methyl-2,4,6-trimethylstyrene Using THF as a Reaction Solvent The same experiment as in Example 4 was carried out, except for using 50 ml of THF instead of 50 ml of CPME. The resulting reaction mixture was analyzed by gas chromatography to confirm that 2-mesityl-2-propanol and α-methyl-2,4,6-trimethylstyrene were obtained in a yield of 44.6% and 33.1%, respectively.

The results of Examples 2-5 and Comparative Example 3-5 confirmed that the target compounds could be produced in a high yield by using the reaction solvent of the present invention.

EXAMPLE 6 Extraction of α,α-dimethylbenzyl Alcohol Using CPME as an Extraction Solvent An aqueous solution obtained by neutralizing the product of Example 2 with hydrochloric acid was charged into a separating funnel. After the addition of 20 ml of CPME and 30 ml of water, the mixture was sufficiently shaken and allowed to stand still for 30 minutes to separate the water layer from the organic layer. The organic layer was removed and stored in a separate vessel. 20 ml of CPME was added to the water layer and the same extraction procedure as above was repeated. The organic layer was removed and put into the same vessel. This extraction procedure was repeated three times. The combined organic layer was washed with a saturated aqueous solution of sodium hydrogencarbonate and water, dried over anhydrous magnesium sulfate, and filtered. The filtrate was concentrated under reduced pressure to obtain 6.4 g of a crude product. The crude product was analyzed by gas chromatography to confirm that α,α-dimethylbenzyl alcohol was obtained in a yield of 71%. In addition, about 99 ml of CPME was collected in the trap of the evaporator (recovery rate of CPME: 90%).

EXAMPLE 7 Extraction of 1-hydroxy-1-phenylcyclopentane and phenylcyclopentene Using CPME as an Extraction Solvent An aqueous solution obtained by neutralizing the product of Example 3 with hydrochloric acid was charged into a separating funnel to carry out the same extraction experiment as in Example 6. 6.8 g of a crude product was obtained. The recovery rate of the target product calculated from the results of gas chromatography analysis of the reaction mixture before extraction procedures was 91%. In addition, about 100 ml of CPME was collected in the trap of the evaporator (overall recovery rate of CPME: 91%).

COMPARATIVE EXAMPLE 6 Extraction of α,α-dimethylbenzyl Alcohol Using Diethyl Ether as an Extraction Solvent An aqueous solution obtained by neutralizing the product of Example 2 with hydrochloric acid was charged into a separating funnel to carry out the same extraction experiment as in Example 6, except that diethyl ether was used as the extraction solvent and the extraction procedure was carried out three times using 20 ml of diethyl ether. 5.5 g of a crude product was obtained. The recovery rate of the target product calculated from the results of gas chromatography analysis of the reaction mixture before extraction procedures was 73%. Almost no diethyl ether was collected in the trap of evaporator.

COMPARATIVE EXAMPLE 7 Preparation of 1-hydroxy-1-phenylcyclopentane and Phenylcyclopentene Using Diethyl Ether as an Extraction Solvent An aqueous solution obtained by neutralizing the product of Example 3 with hydrochloric acid was charged into a separating funnel to carry out the same extraction experiment as in Example 6, except that diethyl ether was used as the extraction solvent and the extraction procedure was carried out three times using 20 ml of diethyl ether. 5.2 g of a crude product was obtained. The recovery rate of the target product calculated from the results of gas chromatography analysis of the reaction mixture before extraction procedures was 73%. Almost no diethyl ether was collected in the trap of evaporator.

The results of Examples 6-7 and Comparative Example 6-7 confirmed a superior extraction effect of the extraction solvent of the present invention. Efficient recovery of CPME used for extraction was also confirmed.

EXAMPLE 8 Fabrication of Information Recording Medium

Cyanine dyes of the following formulas A, B, and C were dissolved in CPME obtained in Preparation Example 1 to obtain coating solutions, each having a dye concentration of 2.0 wt %. The coating solutions were applied to the surface of polycarbonate substrates (outside dimension: 130 mm, internal diameter 15 mm, thickness 1.2 mm, track pitch: 1.6 µm, groove depth: 80 nm) by spin coating (2000 rpm). The coatings were dried at 100° C. for 10 minutes to obtain recording medium layers with a thickness of 0.08 µm.

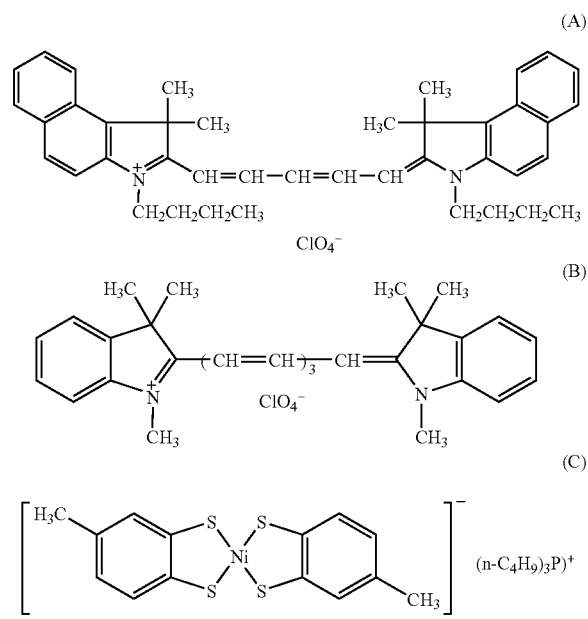

Neither swelling nor dissolution of the polycarbonate resin was observed during the process of forming the recording medium layers (coating and drying). The resulting recording media were checked for recording-reproduction characteristics to confirm that the characteristics were excellent.

EXAMPLE 9 Production of OPC Drum 10 aluminum pipes (thickness: 0.4 mm, diameter: 30 mm, length: 253 mm) were used for the experiment. Notches (width: 2 mm, length: 3 mm) were formed at the ends of the pipes using a 5 kW carbon dioxide laser to obtain drums for preparing OPC drums. 3 parts by weight of X-type metal-free phthalocyanine and 20 parts by weight of 2-butanone were added to and homogeneously dispersed in a solution of one part by weight polyvinyl butyral resin (BM-1, manufactured by Sekisui Chemical Co., Ltd.) in 20 parts by weight of CPME to obtain a coating solution for forming a charge generation layer. The drum was dipped in this coating solution at 25° C. for one minute, removed from the solution, and dried at 100° C. for five minutes in a nitrogen gas stream, thereby forming a charge generation layer with a thickness of 0.25 µm.

Next, 300 parts of N,N'-diphenyl-N,N'-(m-tolyl) benzidine and 64 parts of polycarbonate resin were added to and dissolved in a mixed solvent of CPME prepared in Preparation Example 1 and n-hexane (5:1 by weight), thereby obtaining a coating solution for forming a charge transfer layer. The above drum on which the charge generation layer has been formed was dipped in this coating solution for forming a charge transfer layer at 25° C. for one minute, removed from the solution, and dried at 110° C. in a nitrogen gas stream to form a charge transfer layer on the charge generation layer, thereby obtaining an OPC drum. This procedure was repeated to obtain 10 OPC drums. The charge generation layer of the resulting OPC drums has a uniform thickness (18-19 µm), with only the least defects such as uneven coating.

COMPARATIVE EXAMPLE 9 Production of OPC Drum 10 photosensitive drums were obtained in the same manner as in Example 9, except for using 300 parts of a mixed solvent of THF and n-hexane (5:1 by weight) instead of 300 parts of the mixed solvent of CPME and n-hexane. The charge transfer layer of the resulting OPC drums has a uniform thickness (17-20 µm), with greater unevenness in the coating thickness as compared with the thickness of the charge transfer layer of the OPC drums in Example 9. One photosensitive drum having a charge transfer layer thickness of 17 µm and another drum having a charge transfer layer thickness of 20 µm were regarded as defective products.

EXAMPLE 10 Peeling of Photosensitive Layer from OPC Drum

The two OPC drums evaluated as defective products in Comparative Example 9 were dipped in the mixed solvent of CPME prepared in Preparation Example 1 and n-hexane (5:1 by weight). After 10 minutes, the photosensitive drum was removed from the solution to confirm that the photosensitive layers (charge generating layer and charge transfer layer) were completely peeled from the drum surface and clean drums were recovered. The photosensitive layers can be formed on the recovered drums according to the same procedure as in Example 9.

EXAMPLES 11-12 and COMPARATIVE EXAMPLES 10-11 Test for Releasability of Epoxy Resin Adhesive Specimens for the releasability test were prepared by attaching orientation flat parts of three sheets of 8 inch silicon wafer at intervals of 1 cm on a glass plate (1 cm×6 cm×15 cm) using an epoxy resin adhesive (W-BOND manufactured by Nikka Seiko Co., Ltd.) The epoxy resin adhesive was used by mixing the main component with a curing agent at a ratio by weight of 2:1. The mixture was applied to the glass plate to which the silicon wafer was caused to adhere, cured at 90° C. for one hour, and allowed to stand for 3 hours at room temperature.

The test specimens obtained above were dipped in parting agent solutions listed in Table 4 under the conditions (temperature and supersonic treatment) shown in Table 4. The test specimens were removed from the solutions to determine the period of time required for three sheets of silicon wafer to become detached. The average time for three sheets was regarded as the parting time (minute). A short parting time indicates that only a short period of time was required for removing the epoxy adhesive and the solvent used has excellent parting capability. An ultrasonic irradiation apparatus (Type: SILENT SONICUT-204, 39 kHz, 200 W, 8.6 L, manufactured by Sharp Corp. was used for the ultrasonic treatment.

Parting agents used, dipping temperature (° C.), application of ultrasonic treatment, and parting time (minute) are shown in Table 4.

TABLE 4

|  | Example | | Comparative Example | |
| --- | --- | --- | --- | --- |
|  | 11 | 12 | 10 | 11 |
| Parting agent | CPME | CPME | i-PrOH | BnOH |
| Dipping temperature (° C.) | 70 | 70 | 70 | 70 |
| Ultrasonic treatment | None | Treated | Treated | Treated |
| Parting time (minutes) | 48 | 24 | Over 60 | Over 60 | i-PrOH: iso-propyl alcohol,
BnOH: Benzyl alcohol

It can be seen from Table 4 that the solvent of the present invention exhibits more excellent releasability performance for an epoxy resin adhesive than comparative parting agents (isopropyl alcohol and berizyl alcohol).

PREPARATION EXAMPLE 2

10 g of a commercially available styrene-based acidic ion-exchange resin (RCP 145, water content 46 wt %, manufactured by Mitsubishi Chemical Corp.) was dried in a drier at about 105° C. for 10 hours and then in a desiccator at room temperature for two weeks. The water content of the dry ion-exchange resin was analyzed by Karl-Fischer coulometric titration and found to be 3.0 wt %.

The dry ion-exchange resin was filled in a reaction tube with a diameter of 1" (2.54 cm) and a length of 40 cm. After feeding dry nitrogen gas for five hours at 100° C., the reaction tube was cooled to room temperature. The water content of the resulting dry ion-exchange resin was analyzed by Karl-Fischer coulometric titration to find that water content was 1.5 wt %. The acidic ion-exchange resin (hereinafter referred to as "dry acidic ion-exchange resin") obtained in this manner was used for the reaction.

Hiranuma water content analyzer (AQ-7, manufactured by Hiranuma Industry Co., Ltd.) was used for the determination of water content by the Karl Fischer method. Hydeliner (R) and Aqualite (RS-A) were used as generating solutions and Aqualite (CN) was used as a counter electrode solution.

EXAMPLE 13 Preparation of Cyclopentyl Methyl Ether

A tightly closable reaction vessel (internal volume: 200 ml) made of stainless steel was charged with 3.4 g (0.05 mol) of cyclopentene, 32 g (1.0 mol) of methanol, and 3.0 g of dry acidic ion-exchange resin. After tightly closing the reaction vessel, the mixture was stirred for 6-8 hours at 120° C. under a pressure of 2.5 Mpa. After the reaction, the reaction vessel was opened and the reaction mixture was analyzed by gas chromatography to confirm that the conversion rate of cyclopentene was 30%.

Insoluble matters were separated from the reaction mixture by filtration. The resulting filtrate was distilled under atmospheric pressure using a Vigreux rectifying column to obtain cyclopentyl methyl ether in an isolation yield of 27%.

COMPARATIVE EXAMPLE 12

The same experiment as in Example 13 was carried out, except for using an acidic ion-exchange resin with a water content of 46 wt % (RCP145, manufactured by Mitsubishi Chemical Corp.) instead of the dry acidic ion-exchange resin. The resulting reaction mixture was analyzed by gas chromatography to confirm that the conversion rate of cyclopentyl methyl ether was only 0.4%.

In the same manner as in Example 13, insoluble matters were separated from the reaction mixture by filtration. The resulting filtrate was distilled under atmospheric pressure using a Vigreux rectifying column to obtain cyclopentyl methyl ether in an isolation yield of 0.3%.

COMPARATIVE EXAMPLE 13

A tightly closable reaction vessel (internal volume: 200 ml) made of stainless steel was charged with 3.4 g (0.05 mol) of cyclopentene, 32 g (1.0 mol) of methanol, and 3.0 g of synthetic zeolite catalyst (ZSM-5 manufactured by Mobile R&D Corp.). After tightly closing the reaction vessel, the mixture was stirred for 6-8 hours at 120° C. under a pressure of 1.0 Mpa. The resulting reaction mixture was analyzed by gas chromatography to confirm that the conversion rate of cyclopentyl methyl ether was only 0.07%. Distillation of the mixture in the same manner as in Example 13 failed to isolate the cyclopentyl methyl ether which was only present in a slight amount.

PREPARATION EXAMPLE 3-8

Various acidic ion-exchange resins A1-G1 were dried in the same manner as in Preparation Example 2 to obtain dry acidic ion-exchange resins A2-G2, respectively. The water content of the dry acidic ion-exchange resins was analyzed to find that water content was 1.5 wt % or less for all of them as shown in Table 5.

The sources of the acidic ion-exchange resins A1-G1 were as follows.

Acidic ion-exchange resins A1: SPC108 (manufactured by Bayer AG)

Acidic ion exchange resins B1: SPC118 (manufactured by Bayer AG)

Acidic ion exchange resins C1: PK208LH (manufactured by Mitsubishi Chemical Corp.)

Acidic ion exchange resins D1: PK216LH (manufactured by Mitsubishi Chemical Corp.)

Acidic ion exchange resins E1: PK228LH (manufactured by Mitsubishi Chemical Corp.)

Acidic ion exchange resins F1: Amberlyst 15 (manufactured by Japan Organo Co., Ltd.)

Acidic ion exchange resins G1: RCP145 (manufactured by Mitsubishi Chemical Corp.)

In the following description, the ion-exchange resin produced by drying the acidic ion-exchange resin A1 is called dry acidic ion-exchange resin A2. The same applies to dry acidic ion-exchange resins B2-G2.

EXAMPLES 14-20

The reactor shown in FIG. 1(b) was used in Examples 14-20. The reaction columns 3b, 3c made by SUS with a diameter of 2.54 cm (1") and a length of 40 cm was packed with the above dry acidic ion-exchange resins A2-G2 (amount: about 80 ml). The whole columns 3b, 3c were maintained at 90° C.

A mixture of cyclopentene and methanol (mol ratio: 1.6:1) was sent from a storage tank 1, heated at 90° C. to vaporize in a heater/vaporizer 2b, and continuously charged to the reaction column 3b at a flow rate of 0.8 ml/min at 90° C. under atmospheric pressure. Seven hours after start of the reaction, the reaction liquid flowing from one of the exits of the reaction column 3c was analyzed by gas chromatography.

The reaction solutions extracted from the reaction column 3c during the seven hours after start of the reaction were combined and distilled under atmospheric pressure using a Vigreux rectifying column to obtain cyclopentyl methyl ether. The purity of the resulting cyclopentyl methyl ether was 99% or more.

The type and water content of the dry acidic ion-exchange resin, isolation yield of cyclopentyl methyl ether, conversion rate of methanol, and reaction selectivity of cyclopentyl methyl ether are summarized in Table 5, wherein CPME indicates cyclopentylomethyl ether and MeOH indicates methanol.

COMPARATIVE EXAMPLES 14-20

The same experiment as in Examples 14-20 was carried out, except for using acidic ion-exchange resins A1-G1 with a water content of 40-70 wt % instead of the dry acidic ion-exchange resins A2-G2. The type of the acidic ion-exchange resins, content, conversion rate of methanol, and reaction selectivity are summarized in Table 5. Cyclopentyl methyl ether could not be isolated because the amount produced was too small.

TABLE 5

| | Acidic ion-exchange resin | Water content (wt %) | CPME Yield (%) | MeOH conversion rate (%) | Selectivity (%) |
|---|---|---|---|---|---|
| Example 14 | A2 | 1.5 | 75.5 | 83.6 | 94.9 |
| Example 15 | B2 | 1.5 | 68.9 | 76.2 | 96.2 |
| Example 16 | C2 | 1.5 | 39.9 | 62.2 | 67.5 |
| Example 17 | D2 | 1.5 | 39.4 | 51.9 | 80.9 |
| Example 18 | E2 | 1.5 | 50.1 | 64.1 | 82.4 |
| Example 19 | F2 | 1.5 | 60.0 | 68.3 | 92.5 |
| Example 20 | G2 | 1.5 | 56.2 | 62.7 | 95.3 |
| Comparative Example 14 | A1 | 45-50 | — | 0.7 | 82.3 |
| Comparative Example 15 | B1 | 55-60 | — | 0.6 | 86.5 |
| Comparative Example 16 | C1 | 58-68 | — | 0.5 | 80.2 |
| Comparative Example 17 | D1 | 46-52 | — | 0.3 | 64.3 |
| Comparative Example 18 | E1 | 37-43 | — | 0.4 | 74.3 |
| Comparative Example 19 | F1 | 50 | — | 0.6 | 79.6 |
| Comparative Example 20 | G1 | 46 | — | 0.5 | 75.5 |

As can be seen from Table 5, better results have been obtained for all of the isolation yield of cyclopentyl methyl ether (CPME), the conversion rate of methanol, and the reaction selectivity in the experiments in Examples 14-20 in which dry acidic ion-exchange resins were used than in the experiments in Comparative Examples 14-20 in which acidic ion-exchange resins with a water content of 30-70 wt % were used.

EXAMPLE 21 Preparation of Reaction Solvent

A vessel with a stirrer was charged with 100 parts of CPME obtained in Example 13 and 10 parts of a commercially available dehydrating agent (MS-4A). After stirring for five minutes, the CPME was allowed to stand in the vessel, which was placed at a room temperature in a dry box in which nitrogen gas was circulated, for 18 hours during which change in the water content in CPME over time was measured. The results are shown in Table 6.

2,6-di-tert-butyl-p-cresol was added to the dehydrated CPME to a concentration of 250 ppm. The mixture was stirred to obtain a reaction solvent (hereinafter referred to as "Solvent A") with a water content of 25 ppm.

COMPARATIVE EXAMPLE 21 Preparation of Reaction Solvent

A vessel with a stirrer was charged with 100 parts of a commercially available THF (purity: 99.9%, manufactured by Aldrich Co.) and 10 parts of a commercially available dehydrating agent (MS-4A). After stirring for five minutes, the THF was allowed to stand in the vessel, which was placed at a room temperature in a dry box in which nitrogen gas was circulated, for 18 hours to obtain THF for reaction (hereinafter referred to as "Solvent B"). Change in the water content in THF over time was measured and the results are shown in Table 6.

TABLE 6

| | Water content (ppm) | |
|---|---|---|
| Time (hour) | CPME | THF |
| 0 | 962 | 1024 |
| 0.5 | 391 | 532 |
| 1.0 | 249 | 412 |
| 1.5 | 151 | 310 |
| 2.0 | 98 | 278 |
| 2.5 | 76 | 265 |
| 3.0 | 54 | 258 |
| 4.0 | 44 | 242 |

It can be seen from the results shown in Table 6 that CPME can be dehydrated with MS more easily than THF.

EXAMPLE 22 Synthesis of α,α-dimethylbenzyl Alcohol Using Solvent A 40 parts of a 1 M phenylmagnesium bromide (PhMgBr) solution in Solvent A was added to a flask, of which the atmosphere has been replaced with nitrogen, and stirred at 0° C. for 30 minutes. A solution of 1.74 parts of acetone in 70 parts of Solvent A was slowly added dropwise to the PhMgBr solution at 0° C. After stirring at 0° C. for one hour, the reaction mixture was heated to 50° C. and stirred for a further one hour. After cooling to room temperature, the reaction was terminated with the addition of 20 parts of 1 N hydrochloric acid aqueous solution. The reaction mixture was analyzed by gas chromatography to confirm that the target α,α-dimethylbenzyl alcohol was obtained in a yield of 85%.

50 parts of water was added to partition the mixture into two layers. The organic layer was removed and distilled under atmospheric pressure using a Vigreux rectification column to obtain 99 parts of fractions distilled at 100-106° C. Gas chromatography analysis confirmed that the distillate contained 99% or more of CPME. The distillate can be used again as a solvent.

EXAMPLE 23 Synthesis of α,α-dimethylbenzyl Alcohol Using Recovered CPME

α,α-dimethylbenzyl alcohol was prepared in the same manner as in Example 22 using the CPME recovered in the Example 22 to obtain the α,α-dimethylbenzyl alcohol in a yield of 85%. The experiment confirmed that cyclopentyl methyl ether can be repeatedly used as a reaction solvent.

COMPARATIVE EXAMPLE 22 Synthesis of α,α-dimethylbenzyl Alcohol Using Solvent B

The same experiment as in Example 22 was carried out, except for Solvent B instead of Solvent A. The resulting reaction mixture was analyzed by gas chromatography under the same conditions as above to confirm that the yield of the target compound was only 50%.

EXAMPLE 24 Oil and Fat Solubility Test

The same solubility test as in Example 1 was carried out except for using a cleaning solvent prepared by adding 250 ppm of 2,6-di-tert-butyl-p-cresol to CPME produced in Example 13. The results shown in Table 2 were obtained.

EXAMPLE 25 Peroxide Production Test

A cleaning solvent with the same composition as that used in Example 24 was put into a 20 ml clear glass bottle and allowed to stand at room temperature without shielding from light to observe peroxide production. Peroxides were measured using the iodine ion reduction titration method based on the JIS K9705. The results are shown in Table 7.

TABLE 7

| Time (hour) | Example 16 Peroxide (ppm) |
|---|---|
| 28 | 1 |
| 56 | 5 |
| 84 | 5 |

As is clear from Table 7, the solvent of the present invention is difficult to produce peroxides and thus excels in storage stability.

INDUSTRIAL APPLICABILITY

The solvent comprising the cycloalkyl alkyl ether compound of the present invention (1) can be mixed with various organic solvents and exhibits excellent solubility to fats and oils, waxes, and natural resins, (2) does not adversely affect the ozone layer even if decomposed in the atmosphere due to the absence of halogen atoms such as chlorine and bromine, (3) can be handled with ease as a cleaning solvent due to the moderate boiling point, (4) can be easily recovered after use as a reaction solvent and can produce the target product in a high yield when used in an organic chemical reaction such as a Grignard reaction, and (5) is advantageous from the viewpoint of operational efficiency and environmental safety. Therefore, the solvent of the present invention is useful as a solvent for cleaning electronic and electrical materials, precision machinery components, and the like, as a reaction solvent for various chemical reactions, as an extraction solvent for extracting organic compounds from mixtures, and as a solvent and parting agent for electronic and electrical materials. The target cycloalkyl alkyl ether compound can be advantageously manufactured in an industrial scale according to the manufacturing method of the present invention.

The invention claimed is:

1. A solvent comprising
at least one cycloalkyl alkyl ether compound represented by the formula (1): $R^1$—O—$R^2$, wherein $R^1$ represents a cyclopentyl group and $R^2$ represents an alkyl group having 1-10 carbon atoms or a cycloalkyl group having 3-8 carbon atoms, and an antioxidant.
2. A cleaning solvent comprising a solvent in accordance with claim 1.
3. A reaction solvent comprising a solvent in accordance with claim 1.
4. An organic metal reaction solvent comprising a solvent in accordance with claim 1.
5. A Grignard reaction solvent comprising a solvent in accordance with claim 1.
6. An extraction solvent comprising a solvent in accordance with claim 1.
7. A solvent for electronic or electrical materials comprising a solvent in accordance with claim 1.
8. A parting solvent comprising a solvent in accordance with claim 1.
9. The solvent according to claim 1, having a water content of 100 ppm or less.
10. The solvent according to claim 1, wherein the antioxidant is a phenol antioxidant.
11. The solvent according to claim 1, wherein the antioxidant is 2,6-di-t-butyl-p-cresol.
12. The solvent according to claim 1, wherein the antioxidant is present in an amount of 0.0005-5 weight-% of the total amount of the solvent.
13. The solvent according to claim 1, wherein the peroxide content is below 100 ppm.

* * * * *